United States Patent
Dorn et al.

(10) Patent No.: US 9,403,006 B2
(45) Date of Patent: Aug. 2, 2016

(54) HYBRID FITTING FOR A VISUAL PROSTHESIS

(71) Applicant: Second Sight Medical Products, Inc., San Fernando, CA (US)

(72) Inventors: Jessy D Dorn, Los Angeles, CA (US); Arup Roy, Valencia, CA (US); Robert J Greenberg, Los Angeles, CA (US); Avraham I Caspi, Rehovot (IL)

(73) Assignee: Second Sight Medical Products, Inc., Sylmar, CA (US)

( * ) Notice: Subject to any disclaimer, the term of this patent is extended or adjusted under 35 U.S.C. 154(b) by 0 days.

(21) Appl. No.: 14/752,507

(22) Filed: Jun. 26, 2015

(65) Prior Publication Data

US 2015/0290459 A1 Oct. 15, 2015

Related U.S. Application Data

(62) Division of application No. 13/573,770, filed on Oct. 3, 2012, now Pat. No. 9,089,702.

(51) Int. Cl.
*A61N 1/36* (2006.01)
*A61N 1/05* (2006.01)
*A61N 1/372* (2006.01)

(52) U.S. Cl.
CPC .......... *A61N 1/36046* (2013.01); *A61N 1/0543* (2013.01); *A61N 1/37241* (2013.01); *A61N 1/37247* (2013.01); *A61N 1/37252* (2013.01)

(58) Field of Classification Search
None
See application file for complete search history.

(56) References Cited

U.S. PATENT DOCUMENTS

| | | | |
|---|---|---|---|
| 4,573,481 A | 3/1986 | Bullara | |
| 4,628,933 A | 12/1986 | Michelson | |
| 4,837,049 A | 6/1989 | Byers et al. | |
| 5,109,844 A | 5/1992 | de Juan, Jr. et al. | |
| 5,215,088 A | 6/1993 | Normann et al. | |
| 5,935,155 A | 8/1999 | Humayun et al. | |
| 6,400,989 B1 | 6/2002 | Eckmiller | |
| 6,458,157 B1 | 10/2002 | Suaning | |
| 7,483,751 B2 | 1/2009 | Greenberg et al. | |
| 7,493,169 B2 | 2/2009 | Greenberg et al. | |
| 7,738,962 B2 | 6/2010 | Greenberg et al. | |
| 7,818,064 B2 | 10/2010 | Greenberg et al. | |
| 7,908,011 B2 | 3/2011 | McMahon et al. | |
| 8,180,454 B2 | 5/2012 | Greenberg et al. | |
| 8,190,267 B2 | 5/2012 | Greenberg et al. | |
| 8,195,301 B2 | 6/2012 | Roy et al. | |
| 8,271,091 B2 | 9/2012 | McMahon et al. | |
| 2009/0312818 A1* | 12/2009 | Horsager ........... | A61N 1/36046 607/54 |
| 2010/0057166 A1* | 3/2010 | Ahuja ................ | A61N 1/37247 607/53 |
| 2010/0241192 A1* | 9/2010 | Greenwald ........ | A61N 1/36046 607/54 |

* cited by examiner

*Primary Examiner* — Brian T Gedeon
*Assistant Examiner* — Ankit D Tejani
(74) *Attorney, Agent, or Firm* — Scott B. Dunbar

(57) ABSTRACT

The present invention is an improved fitting and training system for a visual prosthesis. Fitting a visual prosthesis through automated means is challenging and fitting a visual prosthesis manually is tedious for clinician and patent, and provides great opportunity for error. A hybrid of computer controlled and manual fitting provides effective, efficient and controlled fitting process. The process includes testing a group of electrodes in random order by providing a prompt followed by stimulation and the patient responding if they saw a percept. After each set, a maximum likelihood algorithm is used to determine the next stimulation level, or if further stimulation is needed for each electrode.

11 Claims, 28 Drawing Sheets

TABLE 1

| SUBJECT | NUMBER CORRECT | |
|---|---|---|
| | OFF | ON |
| 11-001 | 3 | 13 |
| 11-002 | 2 | 3 |
| 12-001 | 8 | 5 |
| 12-003 | 17 | 12 |
| 12-004 | 4 | 10 |
| 15-001 | 4 | 22 |
| 15-003 | 4 | 17 |
| 17-001 | 4 | 7 |
| 17-002 | 2 | 2 |

FIG. 4

TABLE 2

| SUBJECT | NUMBER CORRECT | |
|---|---|---|
| | OFF | ON |
| 11-001 | 8 | 16 |
| 11-002 | 6 | 18 |
| 12-001 | 7 | 22 |
| 12-003 | 50 | 19 |
| 12-004 | 9 | 9 |
| 15-001 | 7 | 13 |
| 15-003 | 4 | 4 |
| 17-001 | 6 | 9 |
| 17-002 | 2 | 8 |

FIG. 5

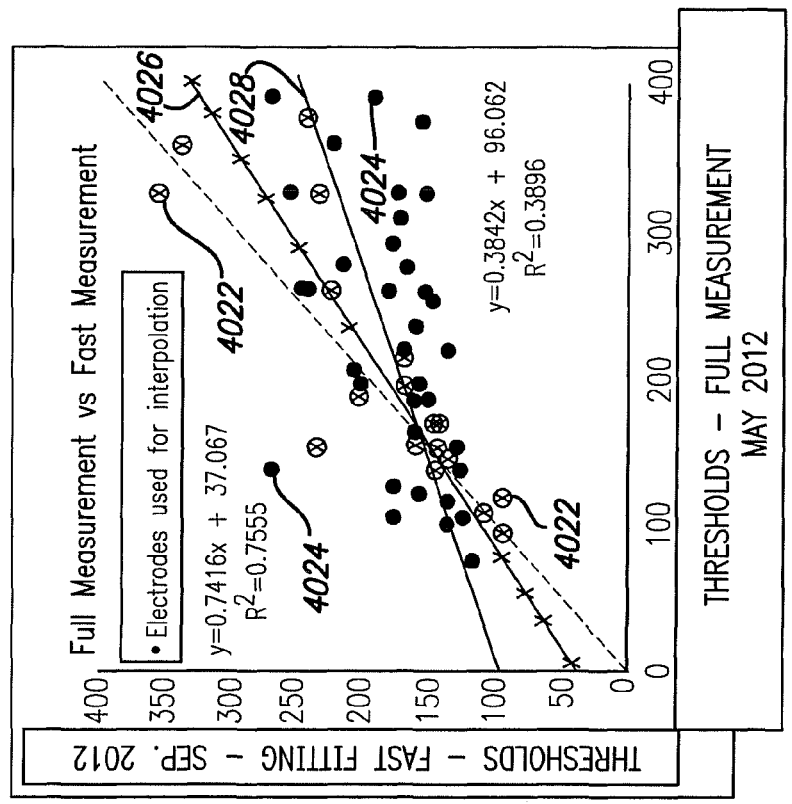
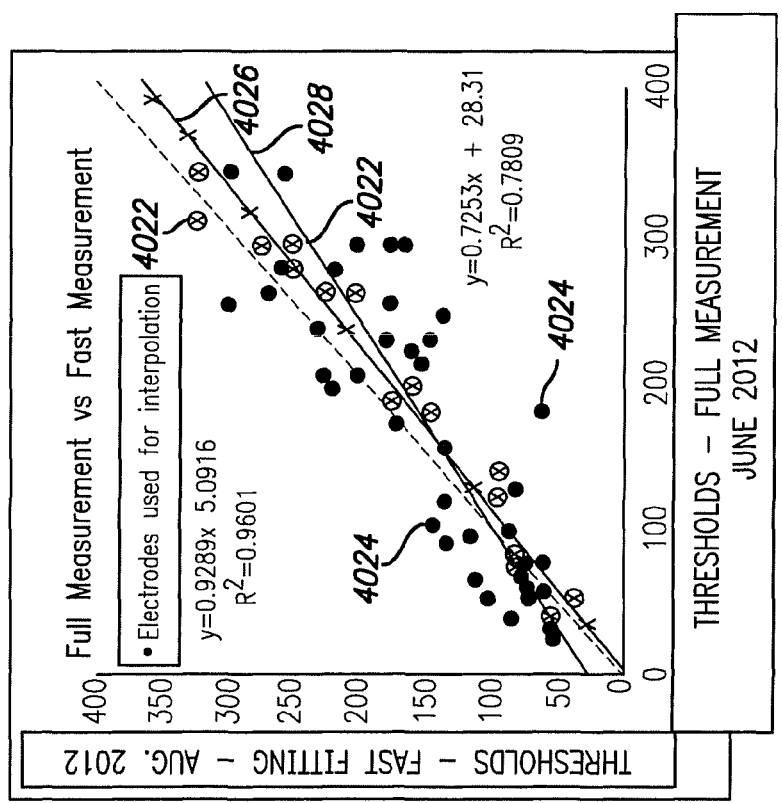
FIG. 21B
FIG. 21A

HYBRID FITTING FOR A VISUAL PROSTHESIS

CROSS REFERENCE TO RELATED APPLICATIONS

This application is a divisional application of U.S. patent application Ser. No. 13/573,770, filed Oct. 3, 2015, for Hybrid Fitting for a Visual Prosthesis.

FIELD

The present disclosure relates to visual prostheses configured to provide neutral stimulation for the creation of artificial vision, and more specifically, and improved method of fitting and training for a visual prosthesis.

BACKGROUND

Ever since 1755 when LeRoy passed the discharge of a Leyden through the orbit of man and caused a visual percept, there has been a fascination with electrically elicited visual perception. The general concept of electrical stimulation of retinal cells to produce these flashes of light or phosphenes has been known for quite some time. Based on these general principles, some early attempts at devising a prosthesis for aiding the visually impaired have included attaching electrodes to the head or eyelids of patients. While some of these early attempts met with some limited success, these early prosthetic devices were large, bulky and could not produce adequate simulated vision to truly aid the visually impaired.

In the early 1930's, Foerster investigated the effect of electrically stimulating the exposed occipital pole of one cerebral hemisphere. He found that, when a point at the extreme occipital pole was stimulated, the patient perceived a small spot of light directly in front and motionless (a phosphene). Subsequently, Brindley and Lewin (1968) thoroughly studied electrical stimulation of the human occipital (visual) cortex. By varying the stimulation parameters, these investigators described in detail the location of the phosphenes produced relative to the specific region of the occipital cortex stimulated. These experiments demonstrated: (1) the consistent shape and position of phosphenes; (2) that increased stimulation pulse duration made phosphenes brighter; and (3) that there was no detectable interaction between neighboring electrodes which were as close as 2.4 mm apart.

As intraocular surgical techniques have advanced, it has become possible to apply stimulation on small groups and even on individual retinal cells to generate focused phosphenes through devices implanted within the eye itself. This has sparked renewed interest in developing methods and apparatuses to aid the visually impaired. Specifically, great effort has been expended in the area of intraocular visual prosthesis devices in an effort to restore vision in cases where blindness is caused by photoreceptor degenerative retinal diseases such as retinitis pigmentosa and age related macular degeneration which affect millions of people worldwide.

Neural tissue can be artificially stimulated and activated by prosthetic devices that pass pulses of electrical current through electrodes on such a device. The passage of current causes changes in electrical potentials across visual neuronal membranes, which can initiate visual neuron action potentials, which are the means of information transfer in the nervous system.

Based on this mechanism, it is possible to input information into the nervous system by coding the information as a sequence of electrical pulses which are relayed to the nervous system via the prosthetic device. In this way, it is possible to provide artificial sensations including vision.

One typical application of neural tissue stimulation is in the rehabilitation of the blind. Some forms of blindness involve selective loss of the light sensitive transducers of the retina. Other retinal neurons remain viable, however, and may be activated in the manner described above by placement of a prosthetic electrode device on the inner (toward the vitreous) retinal surface (epiretial). This placement must be mechanically stable, minimize the distance between the device electrodes and the visual neurons, and avoid undue compression of the visual neurons.

In 1986, Bullara (U.S. Pat. No. 4,573,481) patented an electrode assembly for surgical implantation on a nerve. The matrix was silicone with embedded iridium electrodes. The assembly fit around a nerve to stimulate it.

Dawson and Radtke stimulated cat's retina by direct electrical stimulation of the retinal ganglion cell layer. These experimenters placed nine and then fourteen electrodes upon the inner retinal layer (i.e., primarily the ganglion cell layer) of two cats. Their experiments suggested that electrical stimulation of the retina with 30 to 100 uA current resulted in visual cortical responses. These experiments were carried out with needle-shaped electrodes that penetrated the surface of the retina (see also U.S. Pat. No. 4,628,933 to Michelson).

The Michelson '933 apparatus includes an array of photosensitive devices on its surface that are connected to a plurality of electrodes positioned on the opposite surface of the device to stimulate the retina. These electrodes are disposed to form an array similar to a "bed of nails" having conductors which impinge directly on the retina to stimulate the retinal cells. U.S. Pat. No. 4,837,049 to Byers describes spike electrodes for neural stimulation. Each spike electrode pierces neural tissue for better electrical contact. U.S. Pat. No. 5,215,088 to Norman describes an array of spike electrodes for cortical stimulation. Each spike pierces cortical tissue for better electrical contact.

The art of implanting an intraocular prosthetic device to electrically stimulate the retina was advanced with the introduction of retinal tacks in retinal surgery. De Juan, et al. at Duke University Eye Center inserted retinal tacks into retinas in an effort to reattach retinas that had detached from the underlying choroid, which is the source of blood supply for the outer retina and thus the photoreceptors. See, e.g., E. de Juan, et al., 99 Am. J. Ophthalmol 272 (1985). These retinal tacks have proved to be biocompatible and remain embedded in the retina, and choroid/sclera, effectively pinning the retina against the choroid and the posterior aspects of the globe. Retinal tacks are one way to attach a retinal array to the retina. U.S. Pat. No. 5,109,844 to de Juan describes a flat electrode array placed against the retina for visual stimulation. U.S. Pat. No. 5,935,155 to Humayun describes a visual prosthesis for use with the flat retinal array described in de Juan.

In an implantable visual prosthesis system, the array attached to the retina is very rarely centered and perfectly oriented about the center of the visual field. When an implanted individual's eyes are at a neutral forward looking and level gaze, this is where the brain expects to see the image created by the electrical stimulation of the array. If the camera mounted on the subject's head is looking forward and level and the array is superior to the preferred location, this lack of correspondence between the real world scene and the location of perception will result in the image from the scene in the center of the camera image appearing to the subject as being inferior, which can cause confusion in the down stream visual processing systems such as the LGN (thalamus), superior colliculus, and visual cortex. Similar issues arise with temporal and nasal misalignment as well as rotation.

Further, imperfect position of the camera itself relative to the subject's head can cause the same problem.

In order to properly customize a visual prosthesis for each user, the amount of stimulation required to produce visual percepts (the stimulation threshold) must be measured for each electrode or group of electrodes. While many psychophysical methods for (general) threshold measurement exist, they suffer from known flaws, some of which become prohibitive when applied to threshold measurement for a visual prosthesis. For example, the Method of Constant Stimuli is an accurate but extremely inefficient method; its use is impractical for measuring stimulation thresholds for each individual electrode in a multi-electrode prosthesis. Methods of Adjustment suffer from habituation and anticipation errors; to mitigate the errors, multiple measurements must be made for each electrode, rendering the method impractical. Adaptive methods, in which the stimulus intensity is varied according to previous responses, can produce too narrow a range of stimulation intensity, resulting in a limited understanding of the true psychometric function.

Applicants have developed many methodologies for fitting an electrode array to a patient including: U.S. Pat. No. 8,271,091, for Visual prosthesis fitting; U.S. Pat. No. 8,195,301 Video configuration file editor for visual prosthesis fitting and related method; U.S. Pat. No. 8,190,267, for Fitting a neural prosthesis using impedance and electrode height; U.S. Pat. No. 8,180,454, for Fitting a neural prosthesis using impedance and electrode height; U.S. Pat. No. 7,908,011, for Visual prosthesis fitting; U.S. Pat. No. 7,818,064, for Fitting of brightness in a visual prosthesis; U.S. Pat. No. 7,738,962, for Fitting of brightness in a visual prosthesis; U.S. Pat. No. 7,493,169 for Automatic fitting for a visual prosthesis; U.S. Pat. No. 7,483,751, for Automatic fitting for a visual prosthesis. The preceding list includes both manual and automated fitting methods. Both have advantages and disadvantages. What is needed is a method that uses the best advantages of both manual and automatic fitting.

SUMMARY

The present invention is an improved fitting and training system for a visual prosthesis. Fitting a visual prosthesis through automated means is challenging and fitting a visual prosthesis manually is tedious for clinician and patent, and provides great opportunity for error. A hybrid of computer controlled and manual fitting provides effective, efficient and controlled fitting process. The process includes testing a group of electrodes in random order by providing a prompt followed by stimulation and the patient responding if they saw a percept. After each set, a maximum likelihood algorithm is used to determine the next stimulation level, or if further stimulation is needed for each electrode. This invention is a hybrid of a method of constant stimuli and an adaptive method. When applied to the measurement of stimulation threshold in a visual prosthesis, it provides an efficient and accurate estimate of the stimulation necessary to produce a percept on each individual electrode (or group of electrodes).

Further embodiments are shown in the specification, drawings and claims of the present application.

BRIEF DESCRIPTION OF THE FIGURES

FIG. 4 is a table showing accuracy with the device off or on.

FIG. 5 is a table showing accuracy with the device off or on.

FIGS. 14-1, 14-2, 14-3 and 14-4 show an exemplary embodiment of a video processing unit. FIG. 14-1 should be viewed at the left of FIG. 14-2. FIG. 14-3 should be viewed at the left of FIG. 14-4. FIGS. 14-1 and 14-2 should be viewed on top of FIGS. 14-3 and 14-4.

FIGS. 21A and 21B are graphs comparing fast fitting with hybrid fitting.

DETAILED DESCRIPTION

The present invention is an improved fitting and training system for a visual prosthesis. In the preferred embodiment described below, Fitting is performed in a hybrid of computer controlled and manual functions. Computer software guides the clinician through the fitting process to obtain more reliable results.

The Hybrid Threshold program measures the perceptual threshold for electrical stimulation of individual electrodes (or groups of four electrodes called a "quad" using a hybrid between a Method of Constant Stimuli, in which stimulation amplitudes are pre-set for a block of trials, and an Adaptive Method, in which the stimulation amplitude range is chosen for the next block by an adaptive algorithm (a maximum-likelihood adaptive staircase procedure).

The user selects up to six different single electrodes or quads to test in a single run. In each trial, an audio prompt will be followed by stimulation of one of the electrode groups, selected pseudo-randomly out of the six groups, or no stimulation in the case of a catch trial. After the prompt, the patient must respond "yes" if he or she saw a phosphene or "no" if he or she did not. The trials are grouped into blocks—up to five blocks of 12 trials are completed for each electrode group.

After each block, a maximum likelihood algorithm determines the range of the next block of stimulation amplitude values for each electrode group, based on all previous responses. If the confidence interval of the estimated threshold of an electrode group is narrowed to a pre-set level, trials for that electrode will terminate, but trials on the other electrode groups will continue through a maximum of five blocks.

The program includes a "simulation" mode; in this mode, the functionality of the program is exactly the same as in the non-simulation mode, except that user input via the GUI is ignored; instead, the "input" is automatically generated according to pre-set rules.

Figure 1A:
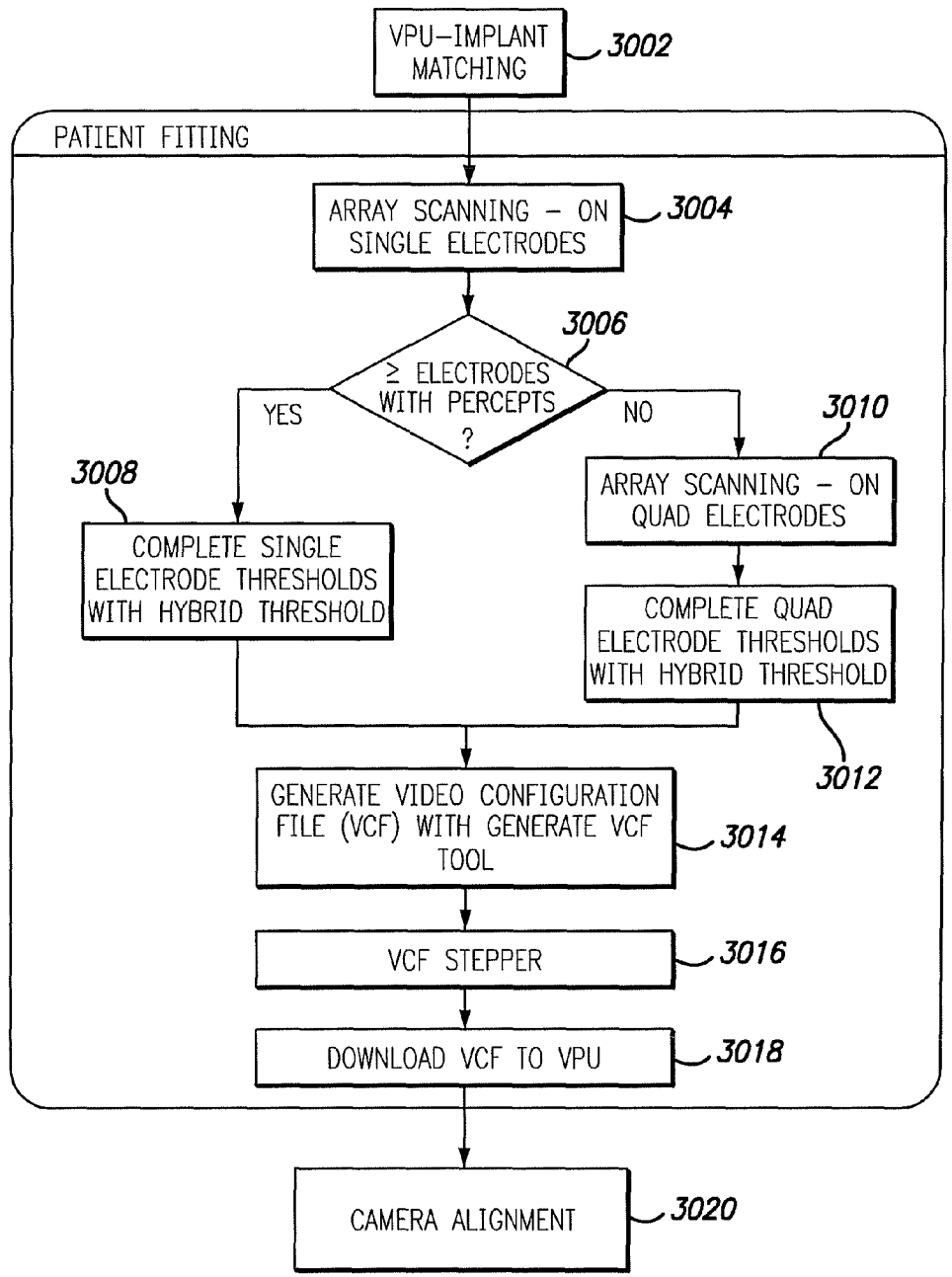
FIGS. 1A and 1B are flowcharts describing the hybrid fitting process.

Referring to FIG. 1A, the fitting process begins with video processing unit (VPU) implant matching. 3002. This automatically checks to insure that the VPU and the video configuration file (VCF) stored on the VPU are properly matched to the implant and not confused with another implant. The next step is array scanning on single electrodes 3004. The ability to obtain a threshold of perception on a single electrode with the safe stimulation level for that electrode, depends on many factors including disease state and array fit. If the system finds thresholds on more than 20 individual electrodes 3006, Then the hybrid threshold process is completed on individual electrodes 3008. If not, array scanning begins again 3010 on four adjacent electrodes in a group, or quads. This allows for stimulation a lower resolution where individual thresholds are not obtained. Then the hybrid threshold process is performed on electrode quads 3012. Then a VCF is created from the hybrid threshold data 3014, the VPU is stepped 3018, and the VCF is loaded on the VPU 3018. The final step is camera alignment 3020.

Figure 9:
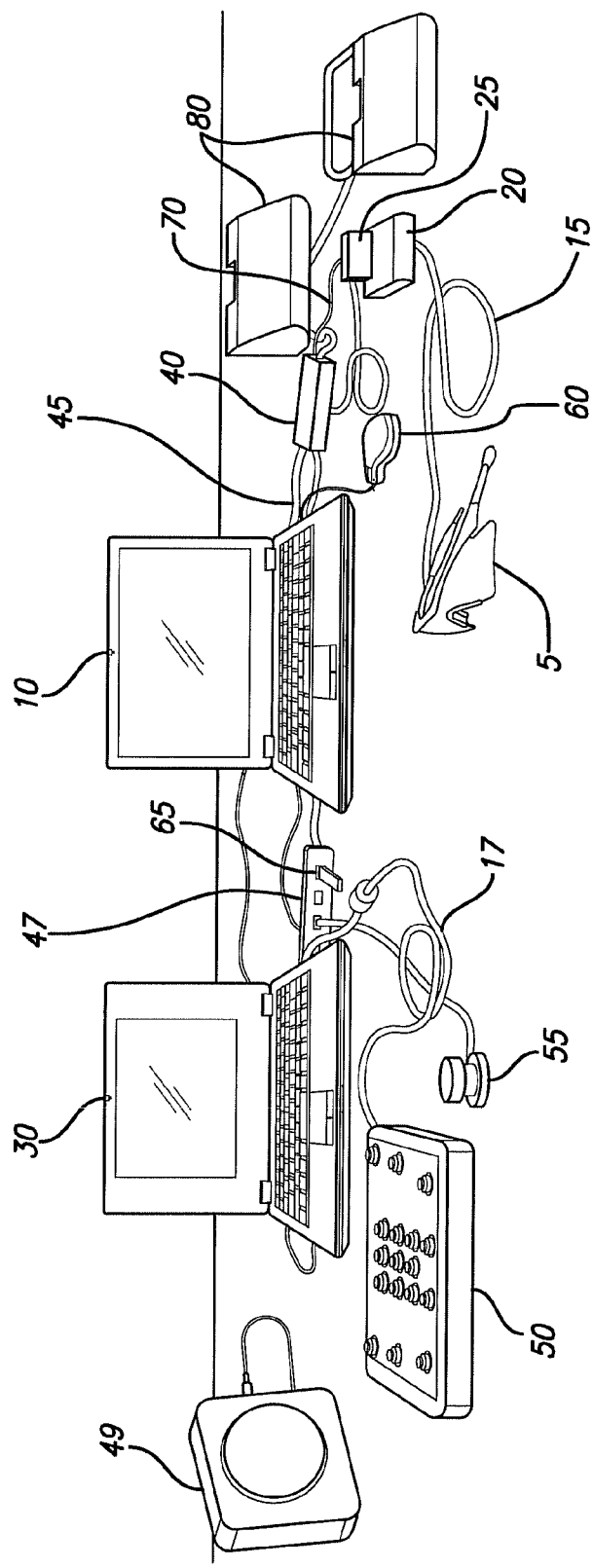
FIG. 9 shows components of a fitting system according to the present disclosure, the system also comprising the visor shown in FIGS. 6 and 7.

To facilitate the subject fitting process, selected psychophysical test scripts have been compiled and integrated into software programs in the clinical fitting system (CFS) a program run on the fitting system laptop (10 in FIG. 9). The installed programs in CFS are Direct Stimulation, Camera Alignment, Array Scanning, Hybrid Threshold, Generate VCF Tool and VCF Stepper. The integrated software programs are described below.

Direct Stimulation:

The Direct Stimulation software program provides an interface on the CFS where the user can enter the configuration parameters, including which electrodes to stimulate, the stimulation amplitude, pulse width parameters, frequency and pulse train duration. The subject's perceptual responses to these direct stimulation experiments provide key inputs to subject fitting process such as camera alignment.

Camera Alignment:

The Camera Alignment software program, used for aligning the camera with the patient's perceptual space, consists of two applications: camera rotation adjustment and camera position (video window) adjustment. The camera rotation adjustment function allows for compensation of the implant electrode array rotation angle for each subject by rotating the camera mounted on the glasses. Prompts provided by the software assist the operator in setting the appropriate rotation angle. The camera position (video window) adjustment allows for the selection of the sub-sampled field of view of the camera that corresponds to the perceptual location resulting from array placement on the retina. The Direct Stimulation program described above and a touch screen monitor are utilized when performing camera alignment.

Array Scanning:

The Array Scanning program is used to determine which electrodes should be tested for thresholds and the appropriate current range to use. Array Scanning stimulates each active electrode up to three times at up to three amplitude levels. The amplitude levels correspond to charge densities of 0.34, 0.66, and 0.99 mC/cm$^2$. Starting with the lowest amplitude, if the subject does not detect phosphenes in at least two out of three stimulations at a given amplitude, the electrode will be stimulated at the next higher amplitude. The program also has the capability of performing array scanning on a group of four adjacent electrodes (referred to as a "quad") where each of the electrodes making up the quad produced no percepts when stimulated individually at the highest amplitude level. Additionally, the Array Scanning program includes the ability for a clinician to exclude one or more electrodes from further measurements if the subject indicates that stimulation on these electrodes produce discomfort. All data are automatically recorded by the CFS.

Figure 1B:
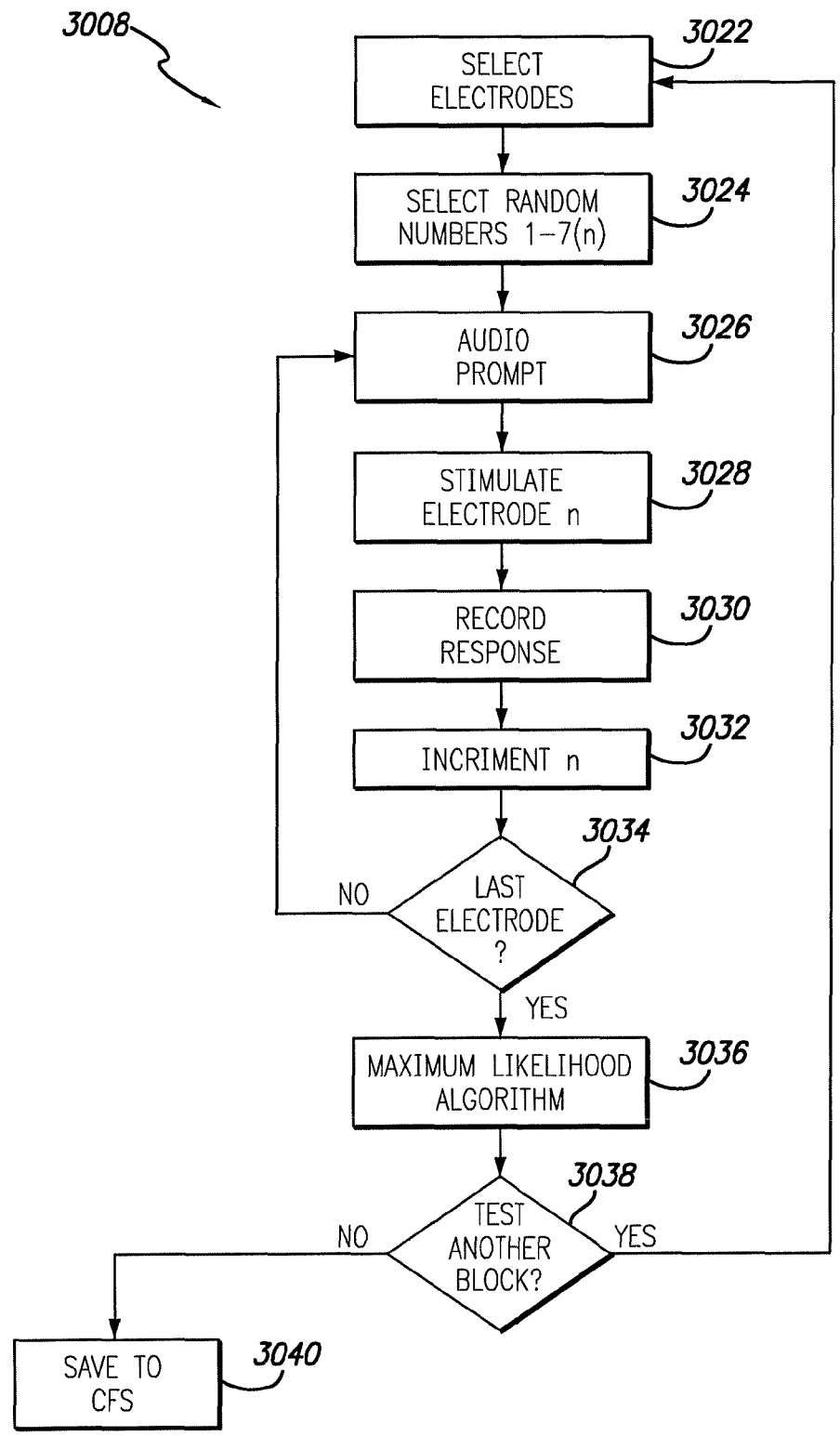
Figure 2A:
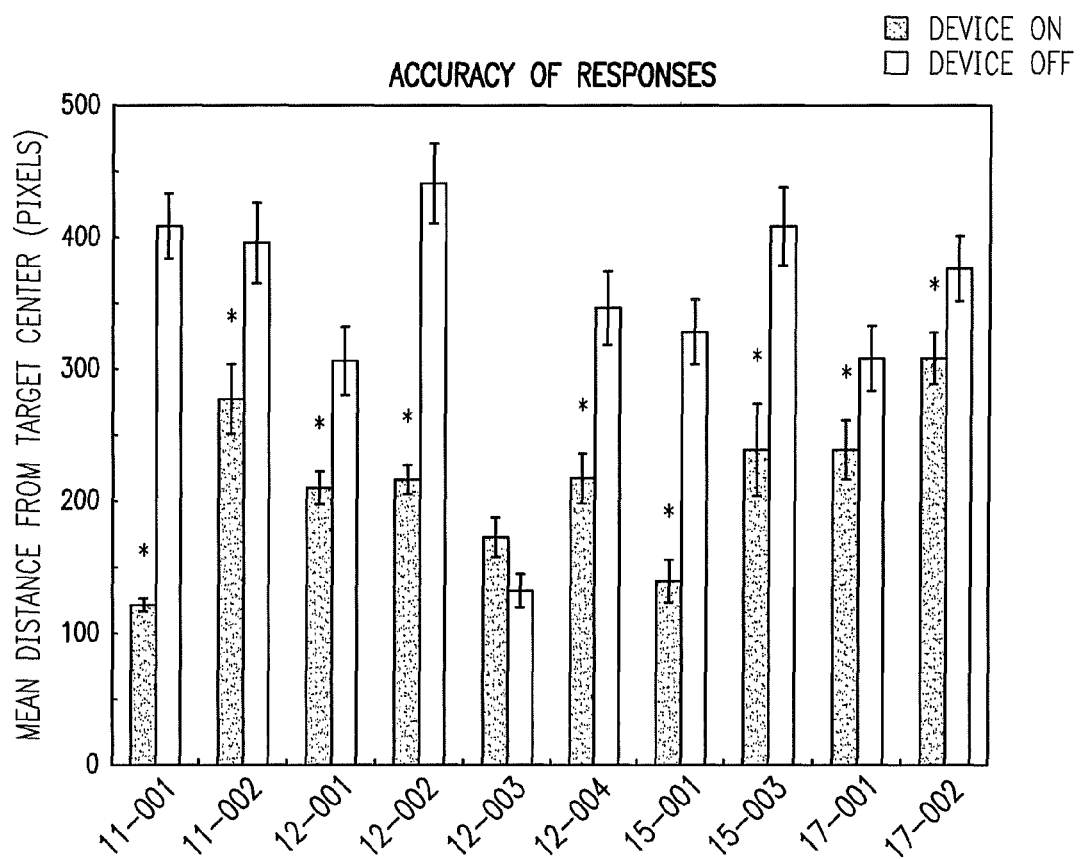
FIGS. 2A and B are a series of bar graphs showing accuracy versus distance.
Figure 2B:
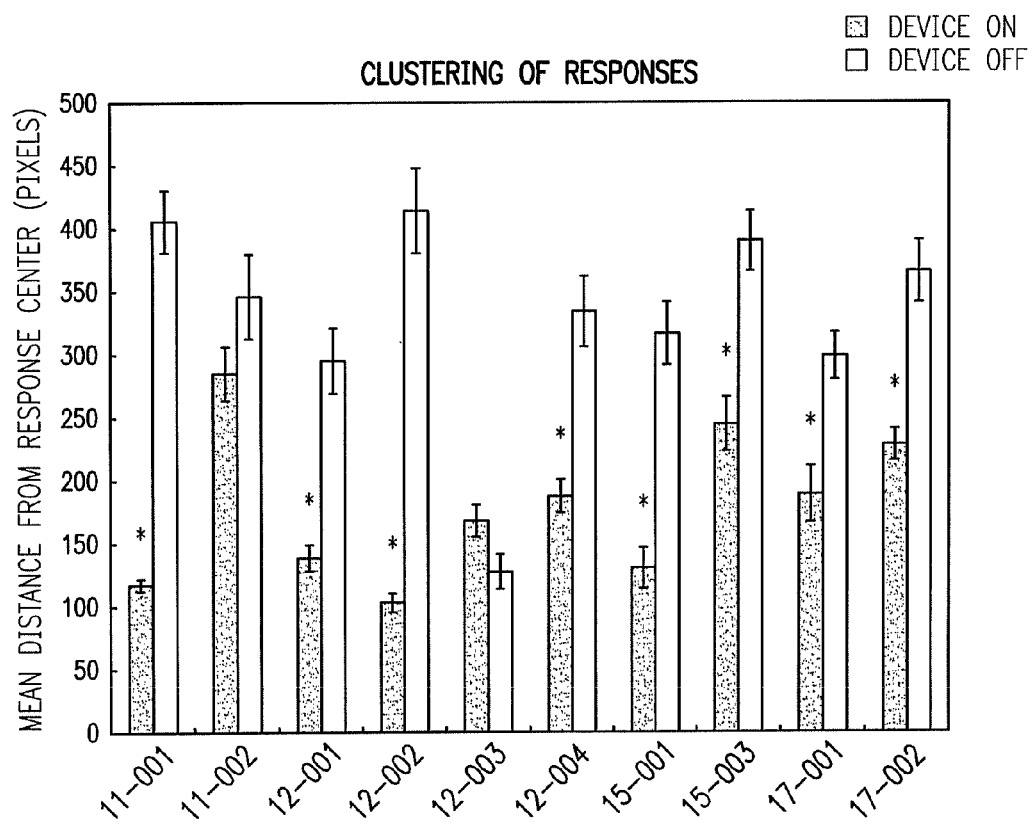

Hybrid Threshold:

The Hybrid Threshold program is used to measure the perceptual threshold for electrical stimulation of individual electrodes by employing an adaptive algorithm. The program can also be configured to measure thresholds for quads (i.e., group of four electrodes). Referring to FIG. 1B, the clinician selects up to six different single electrodes (or quads) to test in a single run 3022. In each trial, an audio prompt 3026 will be followed by stimulation of one of the electrode groups 3028, selected randomly out of the six groups 3024, or no stimulation in the case of a catch trial. After the prompt, the subject responds in the affirmative if he/she saw a phosphene or in the negative if he/she did not 3030. After each response the trial automatically moves to the next electrode 3032 until all electrodes have been tested 3034. The trials are divided into blocks—up to five blocks of 12 trials are completed for each electrode group. After the first block, a maximum likelihood algorithm 3036 determines the range of the next block of stimulation amplitude values for each electrode group, based on all previous responses. If the confidence interval of the estimated threshold of an electrode group is narrowed to a pre-set level, trials for that electrode will terminate 3038, but trials on the other electrodes will continue through a maximum of five blocks. All data are automatically recorded by the CFS 3040.

Amplitude Levels at the First Block

In the first block, under default conditions, there are eight trials with the following amplitudes: 24, 40, 56, 73, 93, 121, 153, and 194 µA. The stimulation levels in the first block are fixed regardless of the CDL range. However, if the stimulation parameters for the run determine a maximum amplitude lower than 194 µA, only the amplitudes from the above list that are less than the maximum are used. In these cases, there are fewer than eight trials in the first block. For example, if the maximum amplitude according to the CDL and pulse width is 130 µA, there will only be 6 trials in the first block (24, 40, 56, 73, 93, and 121 µA).

Amplitude Levels for the Next Block

After each block the likelihood function is calculated according to the following equation:

$$L_i = \prod_{q=1}^{m} (p_{q,i})^{n_{yes,q}} \cdot (1 - p_{q,i})^{n_{no,q}}$$

Where:

$L_i$ is the likelihood that the threshold value is at level i $p_{q,i}$ is the probability, according to the Psychometric Function, that the patient will perceive a stimulation at level q given that the threshold is at level i $n_{yes,q}$ is the number of Yes responses in all previous presentations (trials) at level q $n_{no,q}$ is the number of No responses in all previous presentations (trials) at level q m is the number of levels in the range—the highest level The 95% range of the likelihood function is the range between levels a and b, for which:

$$\frac{L_a}{\max(L)} = 0.0811;$$

$$\frac{L_b}{\max(L)} = 0.0811$$

Where the slope of the likelihood function at point a is positive ($L_{a+1}-L_a>0$) and the slope of at point b is negative ($L_b-L_{b-1}<0$). If the likelihood function doesn't have a negative slope, the level b is set to the highest level in the range (b=m). There will be up to 12 trials at the next block that are set as follows:

1 trial at the amplitude level of the maximum likelihood
1 trial with amplitude level a (left edge of the 95% interval)
1 trial with amplitude level b (right edge of the 95% interval)
4 trials at levels between level a and the level of maximum likelihood. Note: if there are less than
4 levels, then the number of trials will be equal to the number of levels between level a and the level of maximum likelihood.
4 trials at levels between level a and the level of maximum likelihood. Note: if there are less than
4 levels, than the number of trials will be equal to the number of levels between level a and the level of maximum likelihood.
1 trial with amplitude level b+5 (a bright presentation). Note: if b+5>m then the bright trial will be at the highest level (m). In such case, it is possible that there will be 2 trials at the highest level.

Termination Criteria

The criteria to decide that no more trials are necessary for a specific electrode are:

There is no termination in middle of a block. The termination criteria are only implemented between blocks.

If the 95% range of the likelihood function is smaller than 30 µA, then no more trials are necessary on the electrode/quad.

If the 95% range of the likelihood function is smaller than 35% of amplitude of the maximum likelihood, then no more trials are necessary on the electrode/quad.

After 5 blocks—no more trials will be necessary regardless of the range of the likelihood function.

Measured Threshold Value

The value of the measured threshold is the current amplitude with the maximum likelihood based on all trials for the electrode/quad after termination criterion was met.

The measured threshold is the current amplitude level T where $$L_T = \max(L)$$

Because there will always be an amplitude level with maximum likelihood, the criterion in the next section is applied in order to determine if the point with the maximum likelihood is a measurable threshold.

Definition of "A Measurable Threshold"

The amplitude of the stimulation current with the maximum likelihood will be defined as a valid measured threshold in the following cases:

Case #1: There is a peak in the likelihood function, so the level with the maximum likelihood isn't the highest level (T<m). In this case the amplitude level with the maximum likelihood is a valid threshold regardless of the number of Yes responses at that amplitude level.

Case #2: No peak in the likelihood function. The maximum is at the highest limit of the range of amplitude tested in the experiment (T=m). In this case the highest stimulation will be defined as a valid threshold only if there are enough Yes responses at the highest amplitude.

There will be a valid measurable threshold only if the number of "Yes" responses in the two highest stimulation currents is at least 40% of the total number of presentations in the two highest stimulation currents:

$$\frac{n_{yes,m} + n_{yes,m-1}}{n_{yes,m} + n_{yes,m-1} + n_{no,m} + n_{no,m-1}} > 0.4$$

Results that do not fall under Case 1 or Case 2 are defined as having "No Measurable Threshold."

The Fitting Assistant module was introduced to streamline the fitting process. It does not change the methodology for creating video configuration files but simply provides an interface that facilitates the launching of the selected fitting programs (i.e., Array Scanning, Hybrid Threshold, etc.) currently used in the clinical trial. The CFS software (incorporating this module) was evaluated on the bench under simulated use conditions and was determined to meet design specification requirements. As such, clinical validation is not warranted for this update.

Generate VCF Tool:

This software takes the measurements from fitting tests and creates video configuration files (VCFs) that contain the parameters for stimulation that each electrode will deliver. The Generate VCF Tool is automated since it is integrated with the Fitting Assistant module in CFS. As part of the new software release for the CFS, a Fitting Assistant module has been introduced. This module, modeled after the nonnative fitting process performed during subject testing, provides a streamlined, standardized workflow driven process for fitting the subject. When employed, the fitting system module provides an interface that facilitates the launching of selected "fitting utilities" (Array Scanning, Hybrid Threshold, and Generate VCF Tool) included on the CFS platform. It also provides a backend database that these utilities can use to pull results from other files as well as save their results.

Using the fitting assistant model, clinicians can save the results from a fitting test to a database which subsequent fitting utilities will query to obtain the particular data needed for the next step in the fitting process. All of this is managed by CFS which through the user interface will present each fitting utility to the clinician in a standardized workflow. Each of these utilities supports a special "use fitting assistant" mode that indicates use of the database back end. This workflow consists of the following: Array Scanning is run first, and tests for percepts, resulting in a suggested current range for each electrode for measuring thresholds. Once Array Scanning has been completed, Hybrid Threshold is run next, and uses the data generated by Array Scanning to configure itself. After all electrodes have been evaluated for thresholds, a video configuration file (VCF) is generated using the Generate VCF Tool. The Fitting Assistant tab in patient testing displays a button for each of these 3 tools (i.e., fitting utilities) and will only allow the user to select the tools that are available at that point (e.g., if array scanning has not been performed, hybrid threshold will not be made available, as array scanning is a prerequisite for hybrid threshold). As such, the Fitting Assistant module ensures that each step of the fitting process is performed.

It is important to note that when employing the fitting utilities within the Fitting Assistant module most of the fitting parameters are fixed and cannot be modified by the user (e.g., when employing the Array Scanning program inside the Fitting Assistant module, stimulation frequency cannot be modified). As previously indicated, the Fitting Assistant module is based on the normative case for fitting and it was decided during its development that certain parameters be left unsettable for clinicians to account for varying levels of clinician experience. Each of these fitting utility programs, however, has an advanced mode that can be run outside the Fitting Assistant module that allows more experienced users to set these fitting parameters. When running the fitting utilities outside the Fitting Assistant module of CFS, the user does not have access to the backend database.

Camera alignment is correction for rotation and field of view to make the stimulation match the patient remaining vision, if any this is best accomplished through square localization and direction of motion feedback testing as described below.

Square or Circle Localization:

In the Square Localization test, a high-contrast white square (200×200 pixels) was presented in random locations on a 20" touch screen monitor in front of the subject. When prompted, the subject scanned the monitor and located the square, touching the screen at the location of the square center. Subjects first completed a short practice run (10-trial) in training mode, in which they selected the location of the square by touching the monitor where they wanted it to appear. Next, a 40-trial test was administered. No feedback was given to the subject during the test.

Figure 15:
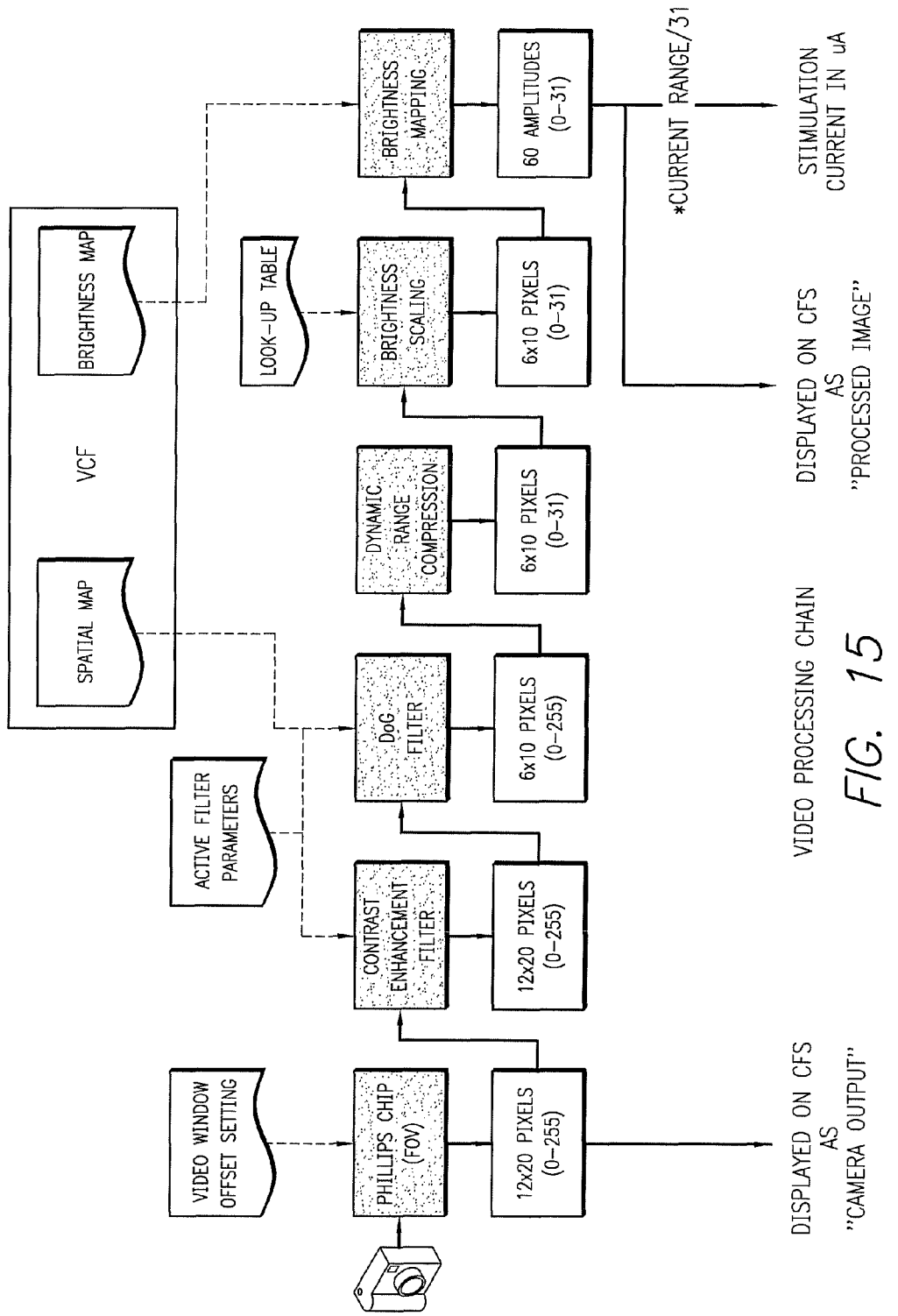
FIG. 15 is flow chart of the video processing chain in a visual prosthesis

The mean and standard deviation from the square localization assessment can be used to adjust the field of view of the camera. This can be done by physically moving the camera angle with respect to the glasses or translating the camera position with respect to the glasses. This can also be done electronically by selecting the appropriate field of view from the camera signal to feed to the implant. Because the image captured by the camera and stored in memory is much larger than the field of view associated with the electrode array on the retina, electronic control can be accomplished by down-selecting an appropriate window of video data from the image. Refer to "Video Window offset Setting" with respect to FIG. 15.

Further, another shape such as circle or square with an intensity that is brightest at the center that gradual fades out may reduce edge effects and measurement error. The size of the shape could be set to the minimum the size that is detectable by the subject, further reducing the measurement error.

The x (horizontal) and y (vertical) location of the mean value of the square localization assessment gives you the apparent location that the patient believes the center of mass of the perceptions are appearing. By correcting for this offset with camera position or field of view position, the patient's perceptions can be aligned with visual stimuli from the monitor. For example, if the mean value was 1 cm to the right of the expected center location, the camera could be angled to the right by 1 cm (or the field of interest could be electronically moved to the right by 1 cm). This, of course, works in the vertical direction too.

Note that the utility of mean, variance and other statistical measures is largely due to the error in measurement that comes from the nature of the task. It has been noted elsewhere that even sighted subjects have a large degree in of error in tasks of this type when they are not able to see their hand as they proceed to point to a target. There are other analyses besides mean and standard deviation that may be more advantageous. For instance, cluster analysis of the data would be helpful when the points fall into more than one region. A moment analysis (center of mass) approach where the pixels were weighted would also improve the precision of the point.

Further, it is also likely that the sources of error sum to locations with a probability density function that is not Gaussian, but rather could have several modes, and it is unlikely that the statistics of the random variables that characterize the measurement error are stationary within an electrode and ergodic over the ensemble of all of the electrodes. Thus non Gaussian distributions can be used to estimate the location of perception. This can include but is not limited to Binomial, Poison with parameter, Geometric with parameter, negative binomial with parameters, and Gamma with parameters. These distribution functions are known in the context of estimation, stochastics, and the characterization or random variables. In the case where the measurement errors are mixed, there will be a central location that is close to the true measurements, and overlapping data from probability distributions of the various error sources. In this case, minimum error classification can be used to select the most likely target to use when adjusting the camera. There are several types of appropriate minimum error classification methods that are known in the art.

A variant on the method discussed above is to make many measurements at one stimulation location and then use the estimated location to physically or electronically move the camera toward this location. This could be done with several other stimulation locations until the difference between the stimulation location and the presented square converge to within an acceptable limit.

In another embodiment, the sum of the errors over all electrodes could be used to set the convergence criterion.

In another embodiment, using the preferred fitting system as shown in FIG. 9, an image may be adjusted manually by the following steps.

1. Be sure the touch screen monitor is connected to the patient testing system (PTS) computer and set to be the primary monitor.

2. Adjust the height of touch screen monitor so that the camera is pointed to the center of the touch screen.

3. Open the fitting software on the PTS laptop, change the directory to the folder containing "Camera Alignment" v1.00, type "runCameraAlignment" and hit Enter. Click on "Camera Position" button. A blank screen will appear on the touch screen.

4. Log in to the clinical fitting system (CFS) and select the "Psychophysics" tab. Log on to PTS and select the "Direct Stimulation" button. Make sure the subject's video processing unit (VPU) is on and connected to CFS and the subject is wearing the glasses.

5. In the PTS "Direct Stimulation" Screen, stimulate a small group of electrodes in the center of the array, and increase the stimulation amplitude and the number of stimulating electrodes until the subject clearly sees localized bright phosphenes.

6. Adjust the subject seating position and the touch screen monitor in order to align the camera to the center of the touch screen and about 12" away from the screen. Instruct the subject to look straight ahead while keeping their head position as still as possible. Use a chin rest if necessary. Generate a phosphene using Direct Stimulation and ask the subject to point the location of the phosphene on the touch screen without moving their eyes or their head. If the position of the phosphene is not on the touch screen, move the touch screen or adjust the height of the subject's chair so that the response is on the monitor. Verify that a gray symbol appears on the touch screen at the location indicated by the subject.

7. Repeat the stimulation and gather a response 8 times. The touch screen will display all the outputs from the subject. Click the "Undo last trial" button to remove the last responses from the subject if necessary. Click the "Back" button to go back to the main screen and click the "Exit" button to exit the program. If the touch screen monitor or the subject seating is adjusted during this step, repeat the step to collect 8 responses.

8. The program will calculate the average position of the responses and present an alignment target (a white circle) centered at this position on the touch screen.

9. Log out of PTS. Select the "CamPos" tab in CFS. Instruct the subject to look straight ahead and to carefully maintain the same head and body position as during the data collection phase. The alignment target should appear in "CamPos" screen. If not, use the right arrow key on the PTS to increase the size of the alignment target until it appears on the "CamPos" screen. Adjust the top, bottom, left, and right arrows on the CFS screen until the alignment target on the touch screen appears at the center of the "CamPos" screen. Reduce the alignment target size if necessary by pressing the left arrow key on the PTS. Click the "save" button on the CFS "CamPos" screen when the alignment target is at the center of the screen. This will select and store the section of the camera image that is aligned with the implant's visual field position on the subject's VPU. Record the saved camera position in the CRF.

10. Run the Square Localization test again to compare with the baseline data.

The ellipse from the square localization assessment is also useful in setting up the field of view of the camera. The area of the ellipse might be used to adjust the zoom of the camera—ie. one might 'zoom out' for a large ellipse or 'zoom in' for a small ellipse. Also, the orientation of the ellipse could be used to adjust the angle or tilt of the camera or field of view. Finally, after adjusting for angle, if the ellipse is not a circle, the ellipse could be used to adjust the horizontal and vertical zoom independently. So, if the ellipse was longer horizontally, a larger horizontal field of view compared to the vertical field of view could be selected.

One additional advantage of the approach is for setting the camera position/field of view is that the entire process can be automated. Thus, a patient can sit in front of a screen that presents individual square stimuli. The patient then touches the touch screen where he/she believes they saw the spot of light. This is repeated for an entire set of locations. The data is then analyzed in real-time (automatically) as described above and automatically downloaded to the VPU to adjust the camera field of view in real-time. In fact, this can be done during the course of the experiment such that data is taken, the field of view adjusted and more data is taken to confirm that the alignment was completed successfully.

Similarly, the direction of motion software can be used to adjust and confirm camera/field of view angle with respect to the horizon. The camera can be rotated (physically or electronically) in real-time until the number of correct responses at zero degrees is maximized. Alternately, the area under the response curve can be integrated and the mean value calculated such that the angle which minimizes the mean value is chosen.

Two spatial vision tests have been developed to supplement Grating Visual Acuity, our primary clinical trial endpoint. These assessment tools, the Square Localization and Direction of Motion tests in the Argus Training Program, were developed to provide an objective measure of spatial vision in subjects who do not reach the lowest levels of the Grating Acuity scale (2.9 log MAR), but who still receive useful spatial information by using the Argus II system. The Square Localization and Direction of Motion tests, device ON and device OFF, were administered to all US Argus II subjects who had been implanted at least 6 months ago (see below for the sole exception).

To determine whether device OFF results were significantly different than device ON results, we considered two measures: accuracy, how close the responses were to the center of the target, and clustering, how close the responses were to the center (mean) of the responses. To measure accuracy, we calculated the distance of each response from the center of the target in pixels for both OFF and ON conditions. A two-tailed Welch's t-test (assuming unequal variances) was then used to determine whether the means were likely to have come from the same distribution (null hypothesis: the means of the OFF and ON distributions are equal). Similarly, to measure the extent of clustering, we calculated the distance of each response from the center (mean) of the responses in OFF and ON conditions and tested the null hypothesis that the means were equal. FIG. 2 shows the mean response distance from the center of the target (FIG. 2-A) or center of the responses (FIG. 2-B) with standard error bars. Statistically different means are indicated with a star (null hypothesis was rejected, $p<0.05$).

In all but one case, the device ON condition resulted in greater accuracy in the Square Localization task than device OFF; the mean response distance from the center of the target was significantly different in OFF and ON conditions for all subjects except 12-003. In addition, most subjects had more tightly clustered responses in device ON than device OFF; only 11-002 and 12-003's ON responses were not significantly more clustered than the OFF.

Figure 3A:
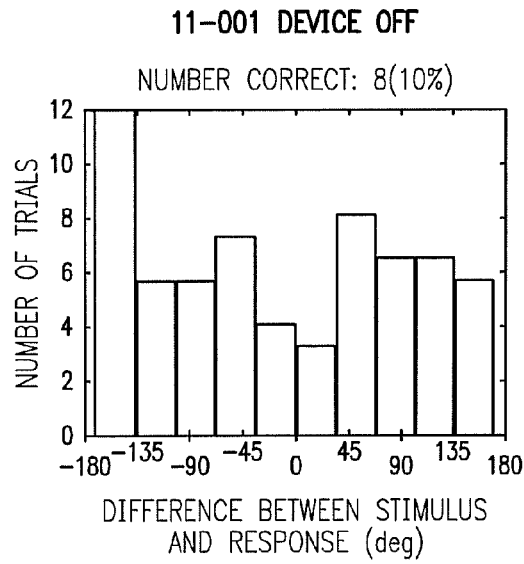
FIGS. 3A-R are a series of bar graphs showing accuracy versus number of trials.
Figure 3B:
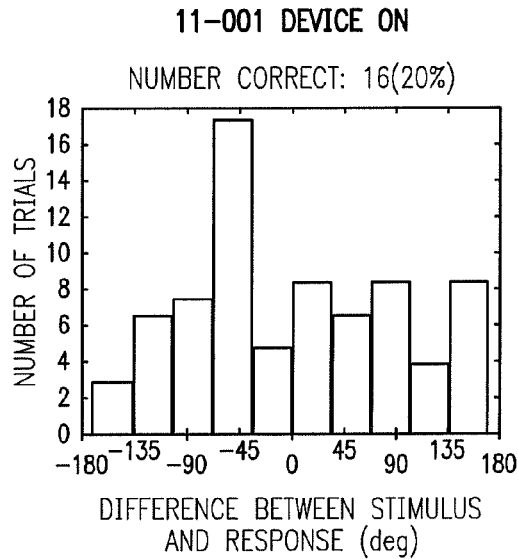
Figure 3C:
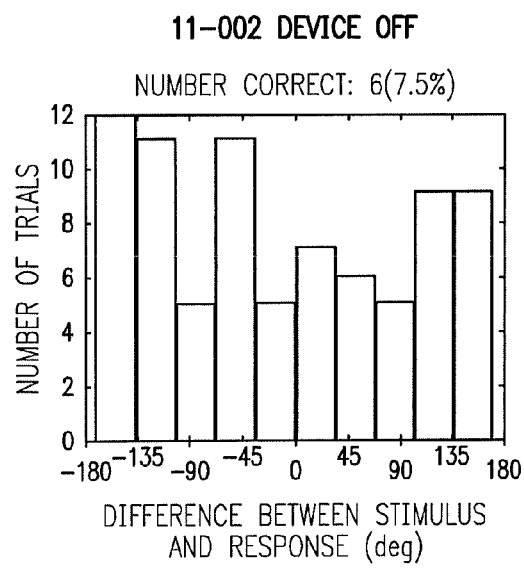
Figure 3D:
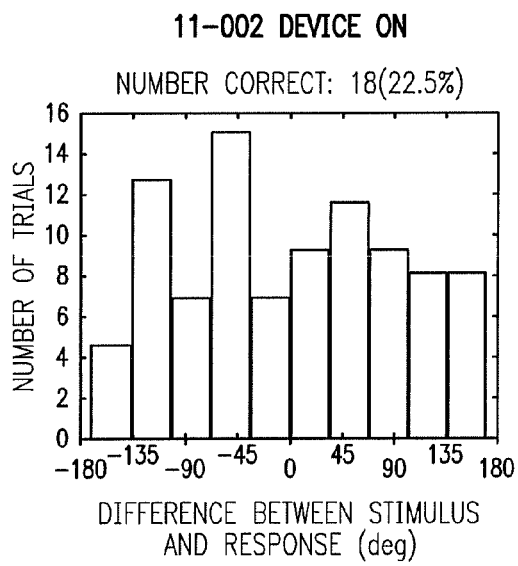
Figures 3E, 3F:
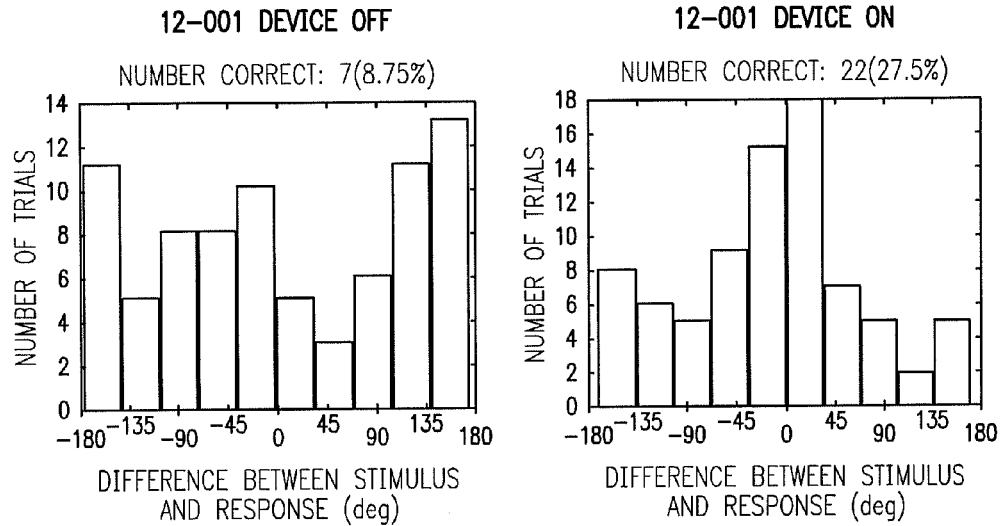
Figures 3G, 3H:
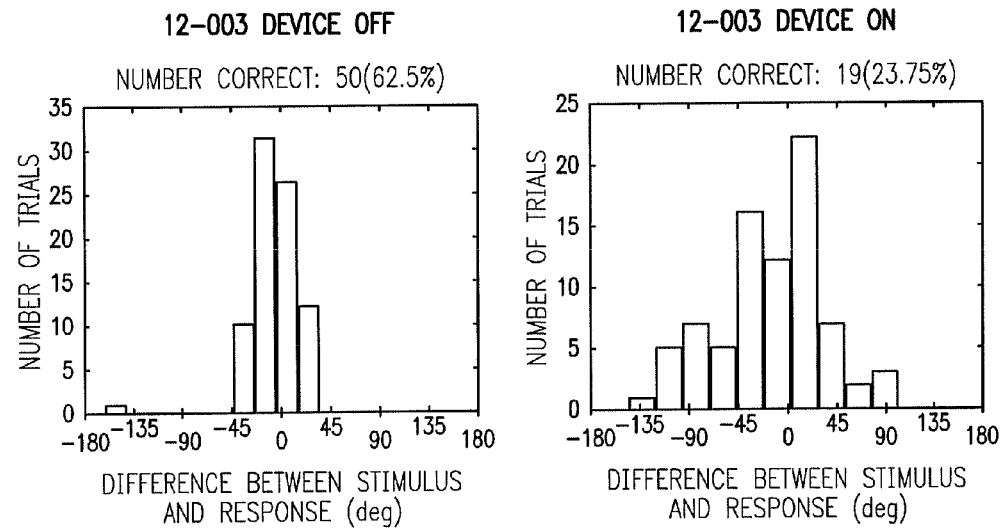
Figures 3I, 3J:
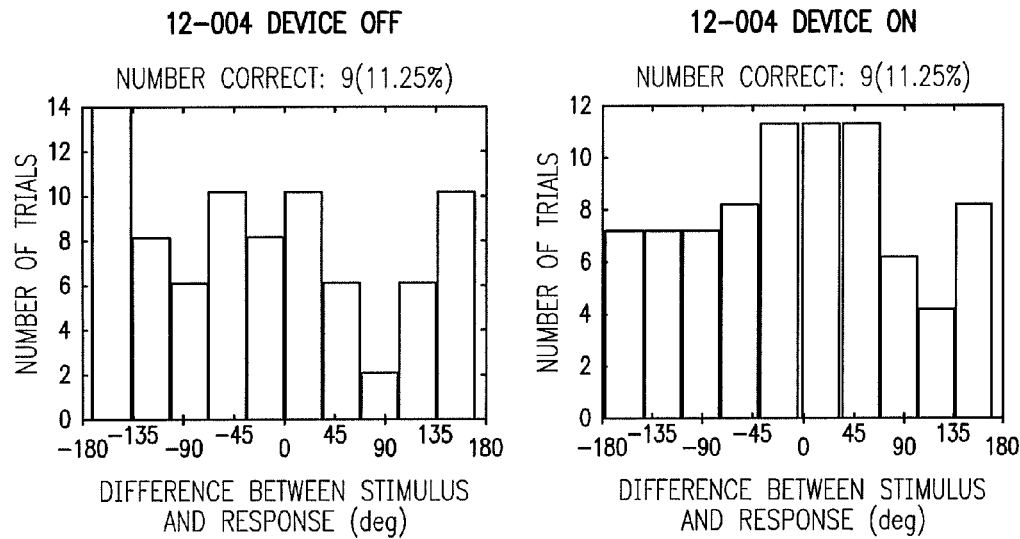
Figures 3K, 3L:
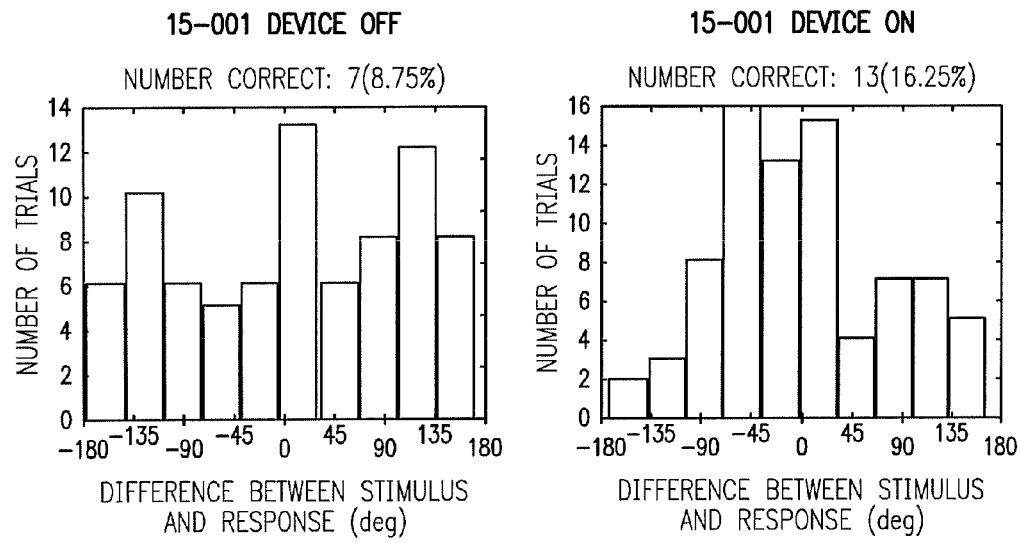
Figures 3M, 3N:
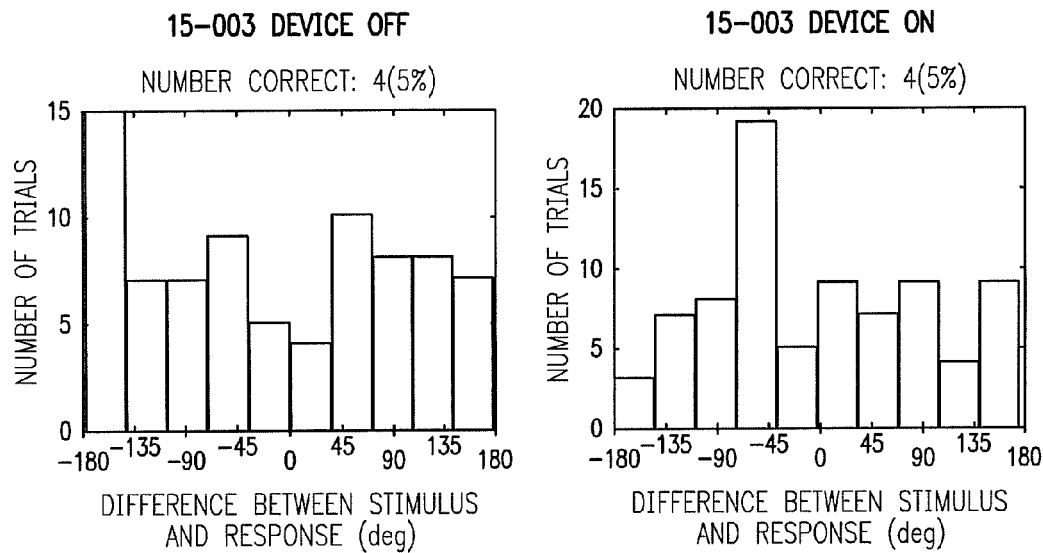
Figures 3O, 3P:
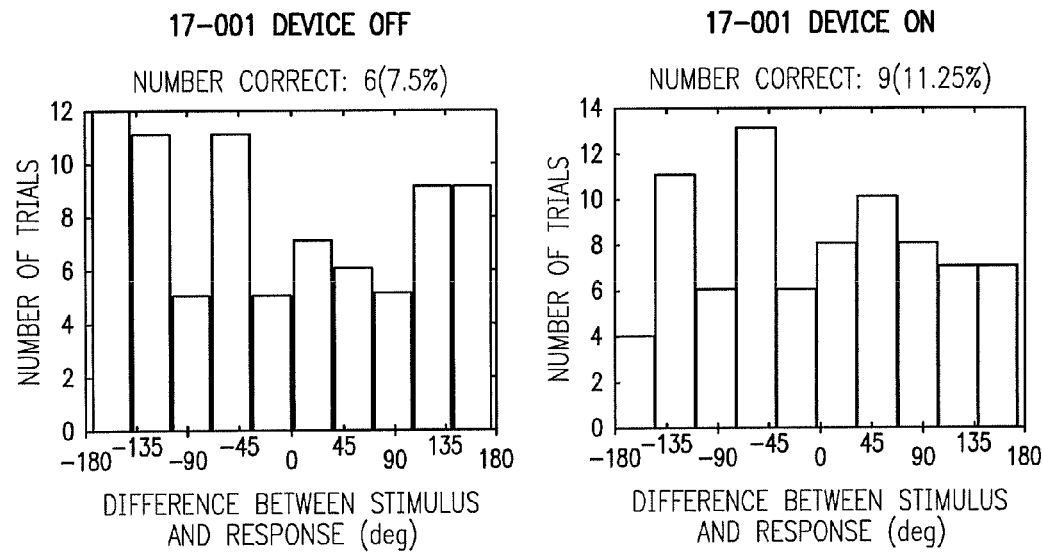
Figure 3Q:
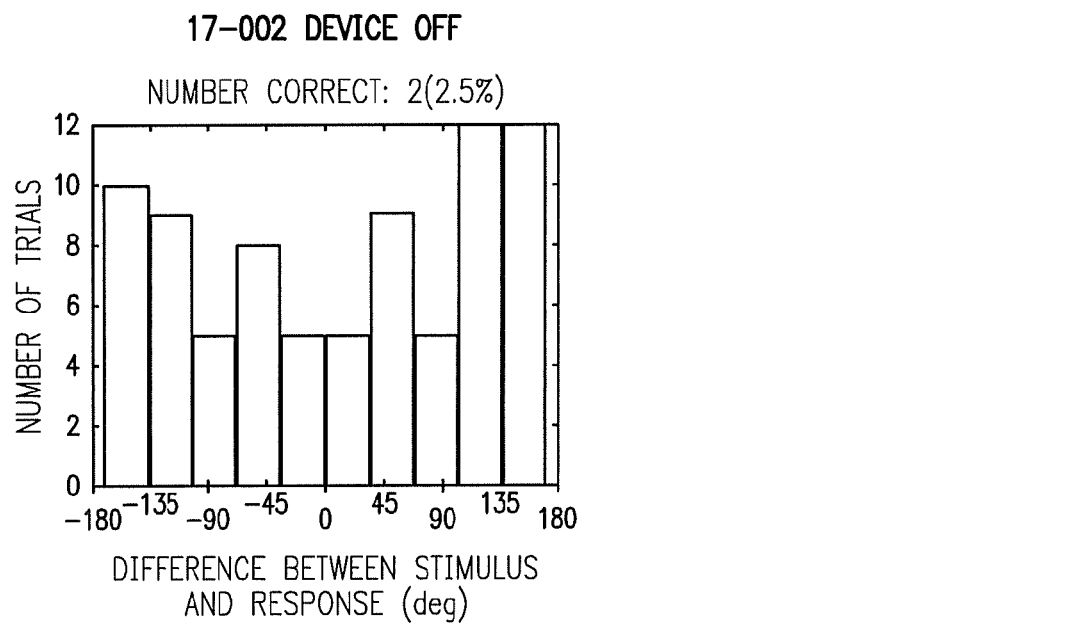
Figure 3R:
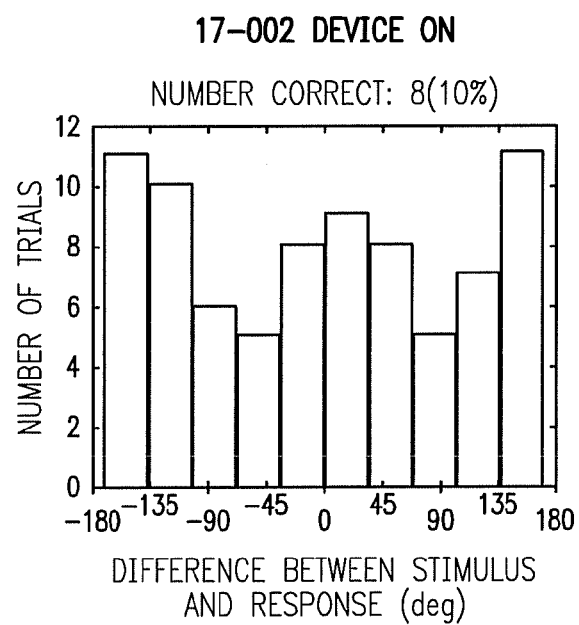

FIGS. 3A-3R provides sample data from specific subjects as described below. In some cases, such as 11-001 and 15-001, the difference between the conditions was very dramatic. 11-001 got 3 correct among many highly-spread responses with device OFF, and 13 correct among responses that were tightly clustered around the square. 15-001 improved from 4 correct with device OFF to 22 correct with device ON.

Several other subjects' performances suggest that their camera alignment should be adjusted—12-001's responses in device ON, for example, were clustered primarily above the target square, while 17-001's were clustered mostly to the bottom right. The new software release A2E6 should allow us to use the information from these experiments to select a better aligned section of the video image.

One subject, 12-003, had better performance in device OFF than ON, though the difference was not statistically significant for either accuracy or clustering in a two-tailed test. Based on this result and subjective analysis of his residual vision, it seems likely that this subject's vision without the device is better than expected.

In the Direction of Motion test, a high-contrast white bar sweeps across a black background on the monitor. The bar's angle was randomly chosen from all 360° (in 1° increments); the bar moved in a direction orthogonal to its orientation angle (for example, a vertical bar moved left to right across the screen). The subjects' task is to fixate the camera on the center of the monitor and allow the bar to sweep across the field of view. They then drew the direction of motion of the bar on the touch screen monitor. After a short training run, an 80-trial test was administered; no feedback was give to the subject during the test. The speed and width of the bar were fixed for all subjects.

Both tests were administered in both device ON and device OFF conditions; for device OFF, the subjects' eyes were both open and they were not wearing their Argus II glasses. For device ON, both eyes were open, but the subject wore their glasses; room lights were off in both conditions. All US subjects were tested between May 13, 2008 and May 30, 2008 except 12-002, who was not tested until August 2008 due to health issues, and 15-003, who was tested in August 2008 when she had been implanted for 4 months.

The following figures show the Direction of Motion results for each subject, device OFF (left) and ON (right). For each trial, the angle difference between the direction of the target bar and the subject's response was calculated; positive angle differences correspond to a counter-clockwise direction, while negative angle differences correspond to a clockwise direction. The angle differences of all 80 trials are shown in a histogram. A star between the device OFF and device ON graphs indicates that the distributions were found to be significantly different ($p<0.05$) with a two-sample Kolmogorov-Smirnov test (null hypothesis: the two distributions are equal).

Correct responses for each condition are summarized in Table 1 (FIG. 4) and Table 2 (FIG. 5); responses were deemed "correct" if the angle difference was +/−15° from the target direction.

It is clear that some subjects are more accurate in judging direction of motion with device on than off. The non-parametric Kolmogorov-Smirnov test found that the device OFF and ON distributions were significantly different in four cases: 11-001, 11-002, 12-001 and 12-003. Indeed, results from three of those subjects (both site 11 subjects and 12-001) show the pattern that we might expect to see—evenly/randomly distributed responses with device OFF, but a distribution that peaks around 0° angle difference with device ON. All three of these subjects also had more correct responses in the ON condition. Subjects 12-004, 15-001, 15-003, 17-001 and 17-002 do not have significantly different results with device ON than OFF. And subject 12-003, again, showed better results with device OFF than ON; the distributions were significantly different according to the K-S test.

Figure 6:
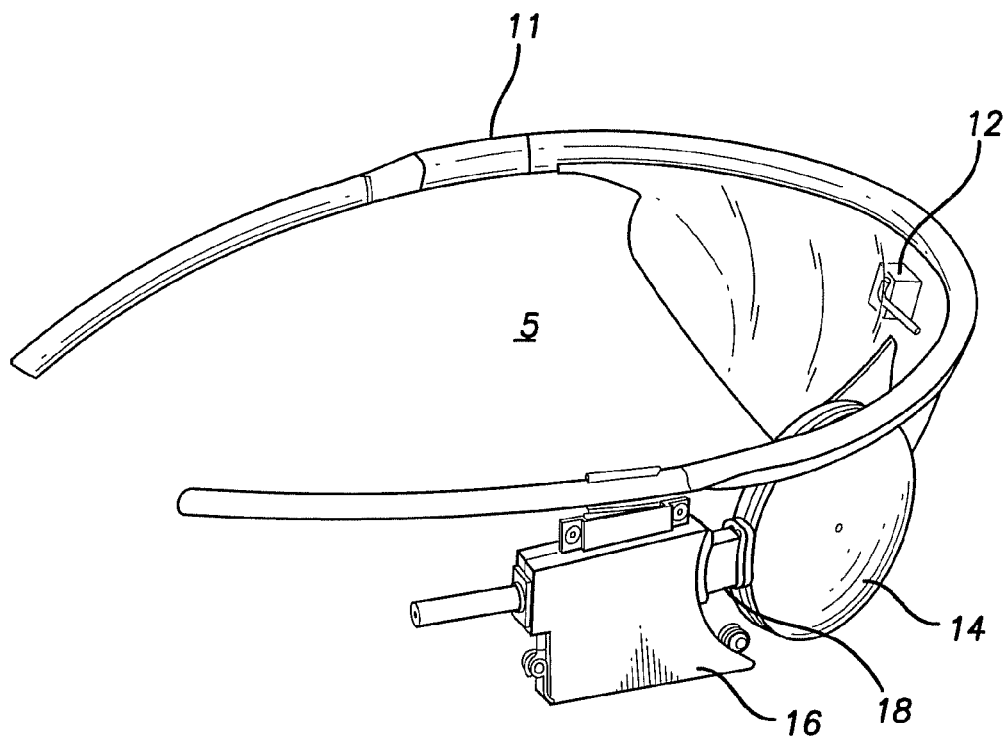
FIGS. 6 and 7 show a video capture/transmission apparatus or visor adapted to be used in combination with the retinal stimulation of FIGS. 16 and 17.
Figure 7:
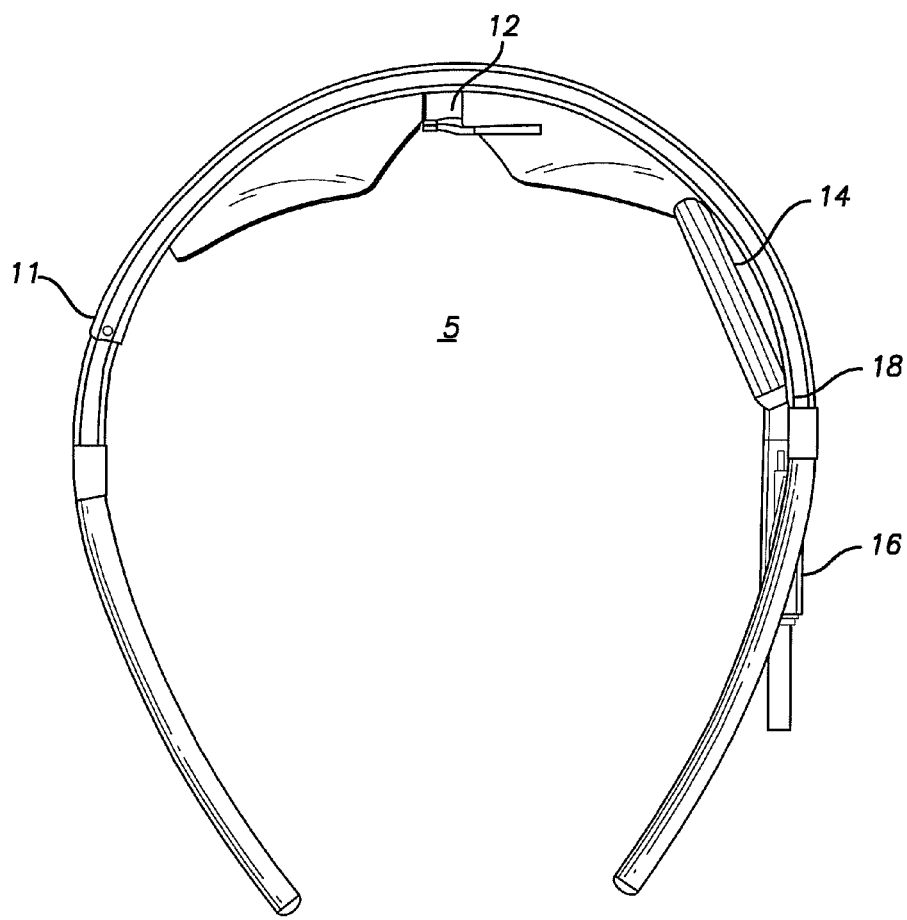
Figure 8:
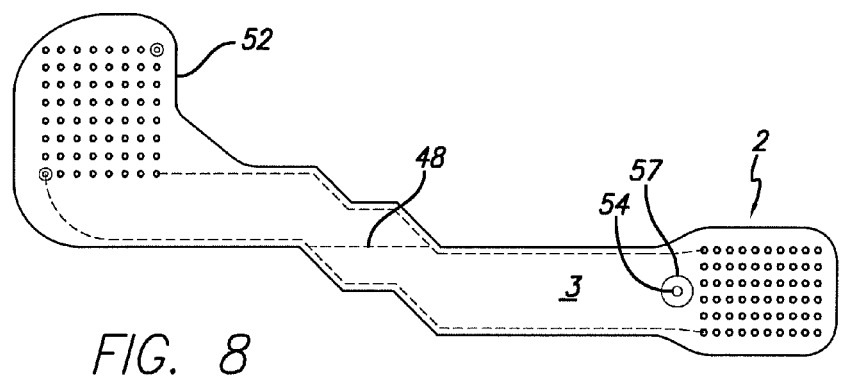
FIG. 8 shows a flexible circuit electrode array.

Referring to FIGS. 6 and 7, the glasses 5 may comprise, for example, a frame 11 holding a camera 12, an external coil 14 and a mounting system 16 for the external coil 14. The mounting system 16 may also enclose the RF circuitry. In this configuration, the video camera 12 captures live video. The video signal is sent to an external Video Processing Unit (VPU) 20 (shown in FIGS. 9, 11 and 12 and discussed below), which processes the video signal and subsequently transforms the processed video signal into electrical stimulation patterns or data. The electrical stimulation data are then sent to the external coil 14 that sends both data and power via radio-frequency (RF) telemetry to the coil 116 of the retinal stimulation system 1, shown in FIGS. 16 and 3. The coil 116 receives the RF commands which control the application specific integrated circuit (ASIC) which in turn delivers stimulation to the retina of the subject via a thin film electrode array (TFEA). In one aspect of an embodiment, light amplitude is recorded by the camera 12. The VPU 20 may use a logarithmic encoding scheme to convert the incoming light amplitudes into the electrical stimulation patterns or data. These electrical stimulation patterns or data may then be passed on to the Retinal Stimulation System 1, which results in the retinal cells being stimulated via the electrodes in the electrode array 2 (shown in FIG. 16). In one exemplary embodiment, the electrical stimulation patterns or data being transmitted by the external coil 14 is binary data. The external coil 14 may contain a receiver and transmitter antennae and a radio-frequency (RF) electronics card for communicating with the internal coil 116.

Figure 16:
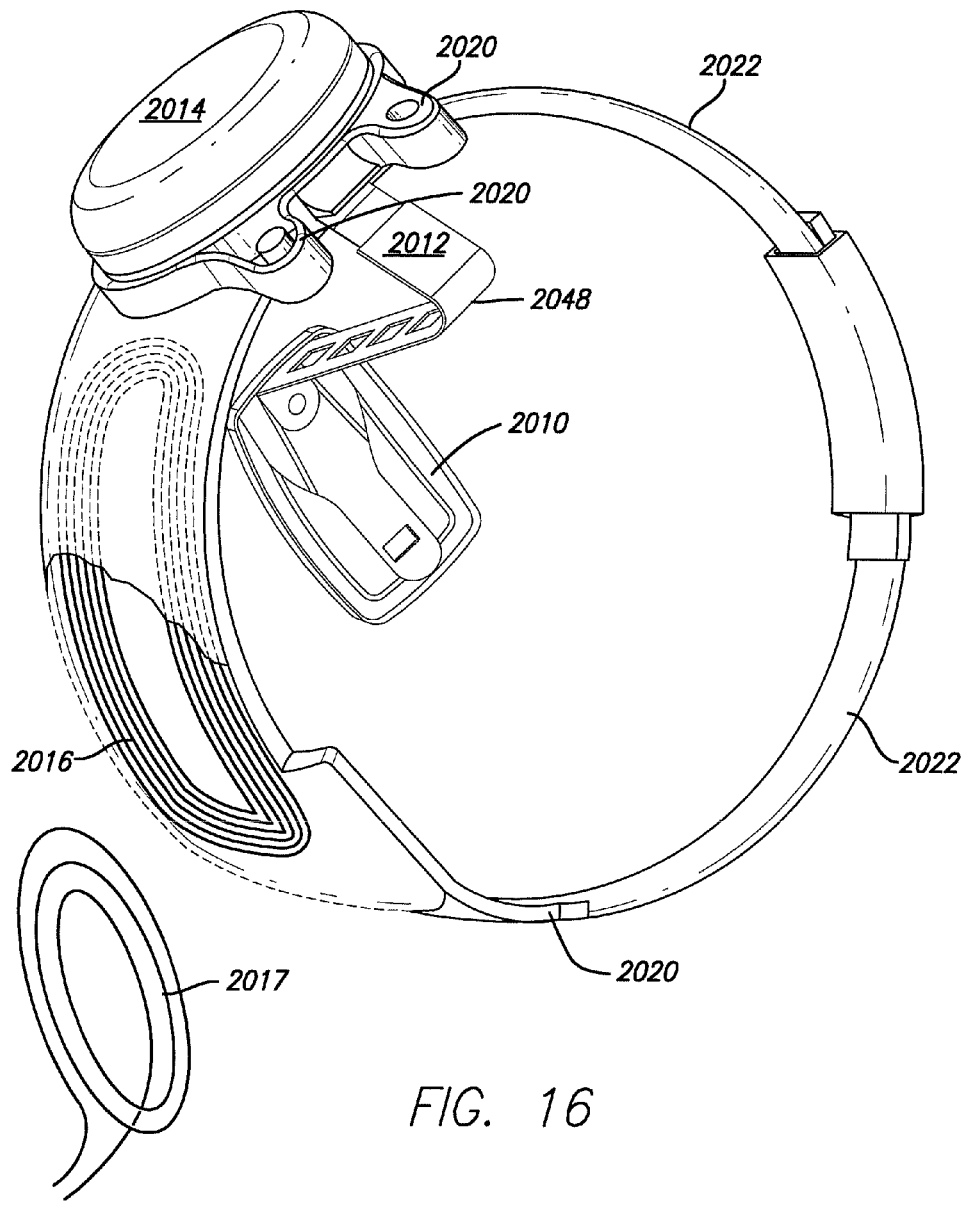
FIG. 16 is a perspective view of the implanted portion of the preferred visual prosthesis.

Referring to FIG. 9, a Fitting System (FS) may be used to configure and optimize the visual prosthesis apparatus shown in FIG. 16. The Fitting System is fully described in the related application U.S. application Ser. No. 11/796,425, filed on Apr. 27, 2007, which is incorporated herein by reference in its entirety.

The Fitting System may comprise custom software with a graphical user interface running on a dedicated laptop computer 10. Within the Fitting System are modules for performing diagnostic checks of the implant, loading and executing video configuration files, viewing electrode voltage waveforms, and aiding in conducting psychophysical experiments. A video module can be used to download a video configuration file to the Video Processing Unit (VPU) 20 discussed above and store it in non-volatile memory to control various aspects of video configuration, e.g. the spatial relationship between the video input and the electrodes. The software can also load a previously used video configuration file from the VPU 20 for adjustment.

The Fitting System can be connected to the Psychophysical Test System (PTS), located for example on a dedicated laptop 30, in order to run psychophysical experiments. In psychophysics mode, the Fitting System enables individual electrode control, permitting clinicians to construct test stimuli with control over current amplitude, pulse-width, and frequency of the stimulation. In addition, the psychophysics module allows the clinician to record subject responses. The PTS may include a collection of standard psychophysics experiments developed using for example MATLAB® (MathWorks)™ software and other tools to allow the clinicians to develop customized psychophysics experiment scripts.

Using the psychophysics module, important perceptual parameters such as perceptual threshold, maximum comfort level, and spatial location of percepts may be reliably measured. Based on these perceptual parameters, the fitting software enables custom configuration of the transformation between video image and spatio-temporal electrode stimulation parameters in an effort to optimize the effectiveness of the visual prosthesis for each subject.

The Fitting System laptop 10 of FIG. 9 may be connected to the VPU 20 using an optically isolated serial connection adapter 40. Because it is optically isolated, the serial connection adapter 40 assures that no electric leakage current can flow from the Fitting System laptop 10 in the even of a fault condition.

As shown in FIG. 9, the following components may be used with the Fitting System according to the present disclosure. The Video Processing Unit (VPU) 20 for the subject being tested, a Charged Battery 25 for VPU 20, the Glasses 5, a Fitting System (FS) Laptop 10, a Psychophysical Test System (PTS) Laptop 30, a PTS CD (not shown), a Communication Adapter (CA) 40, a USB Drive (Security) (not shown), a USB Drive (Transfer) 47, a USB Drive (Video Settings) (not shown), a Patient Input Device (RF Tablet) 50, a further Patient Input Device (Jog Dial) 55, Glasses Cable 15, CA-VPU Cable 70, FS-CA Cable 45, FS-PTS Cable 46, Four (4) Port USB Hub 47, Mouse 60, Test Array system 80, Archival USB Drive 49, an Isolation Transformer (not shown), adapter cables (not shown), and an External Monitor (not shown).

With continued reference to FIG. 9, the external components of the Fitting System may be configured as follows. The battery 25 is connected with the VPU 20. The PTS Laptop 30 is connected to FS Laptop 10 using the FS-PTS Cable 46. The PTS Laptop 30 and FS Laptop 10 are plugged into the Isolation Transformer (not shown) using the Adapter Cables (not shown). The Isolation Transformer is plugged into the wall outlet. The four (4) Port USB Hub 47 is connected to the FS laptop 10 at the USB port. The mouse 60 and the two Patient Input Devices 50 and 55 are connected to four (4) Port USB Hubs 47. The FS laptop 10 is connected to the Communication Adapter (CA) 40 using the FS-CA Cable 45. The CA 40 is connected to the VPU 20 using the CA-VPU Cable 70. The Glasses 5 are connected to the VPU 20 using the Glasses Cable 15.

Figures 1, 14:
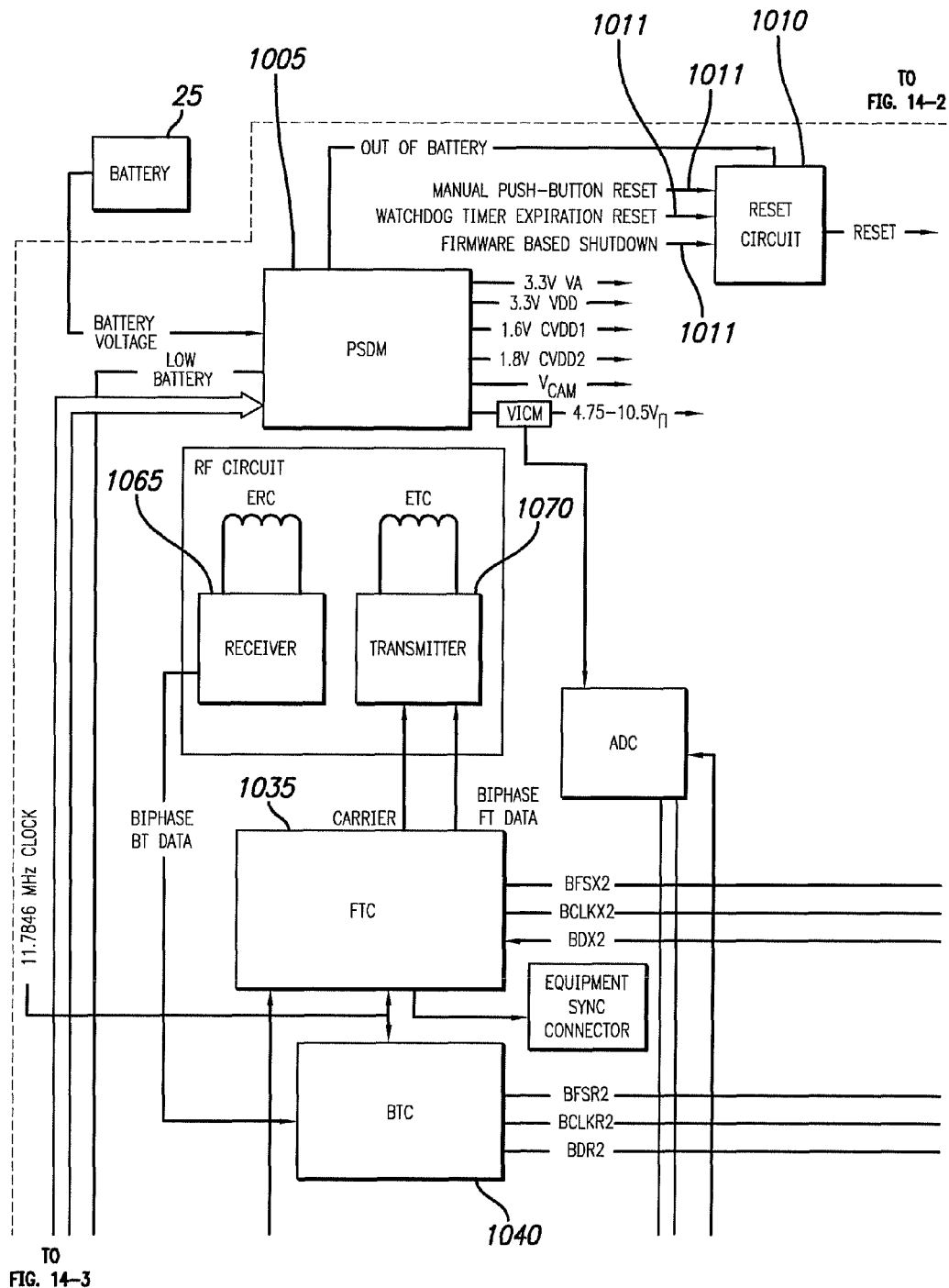
Figures 2, 14:
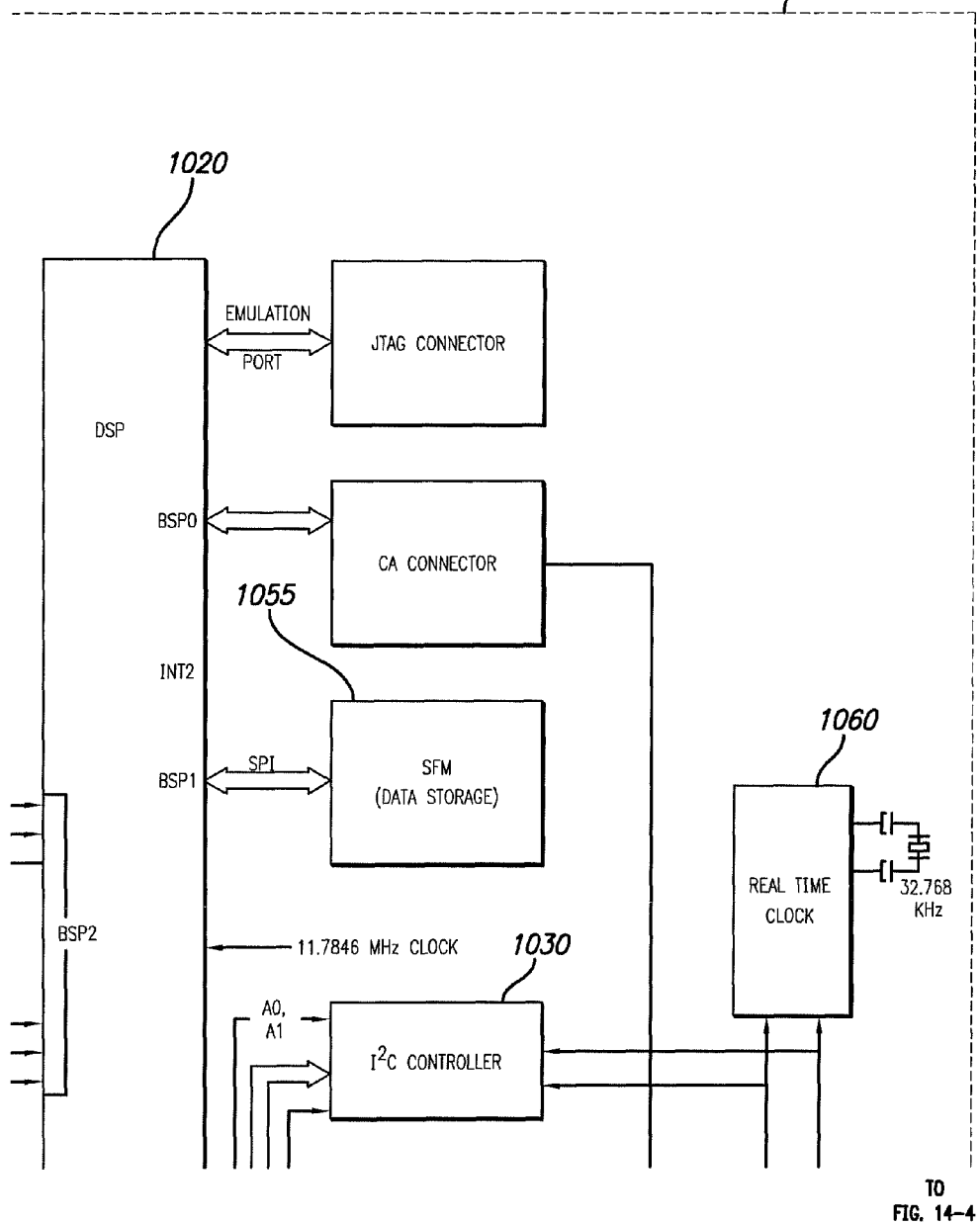
Figures 3, 14:
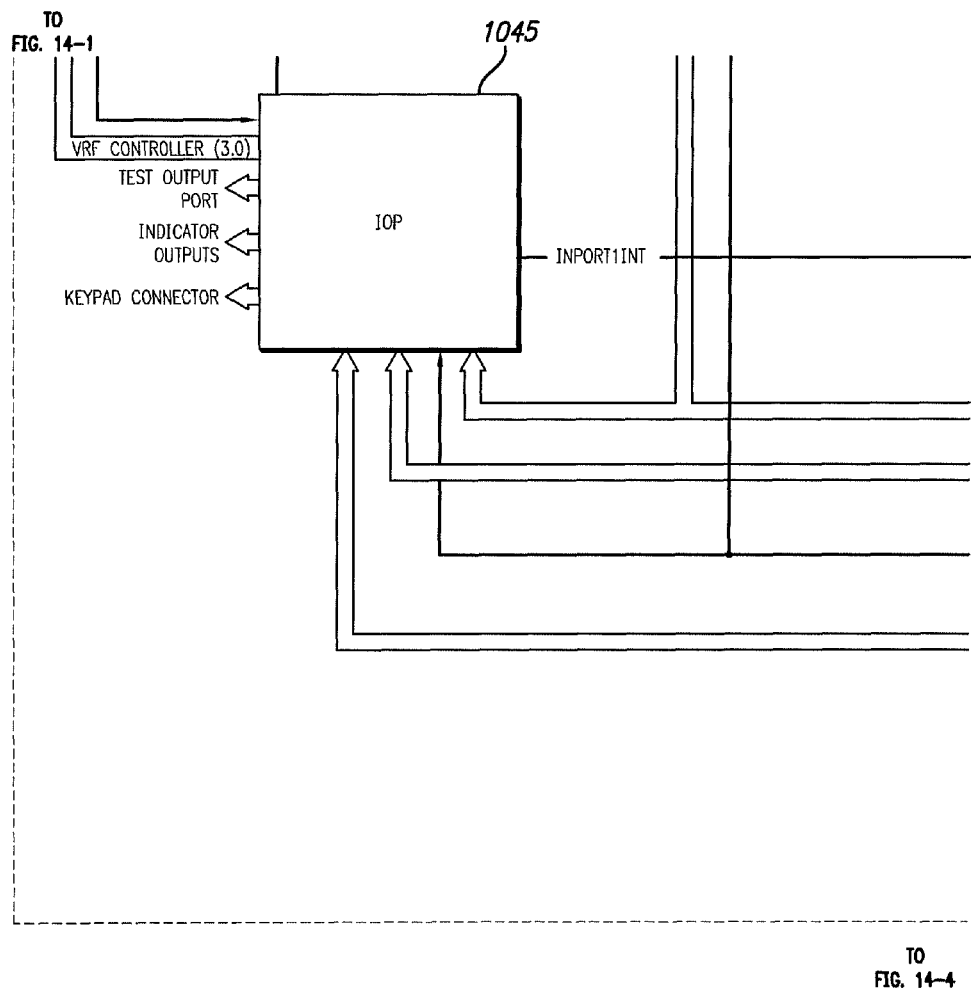
Figures 4, 14:
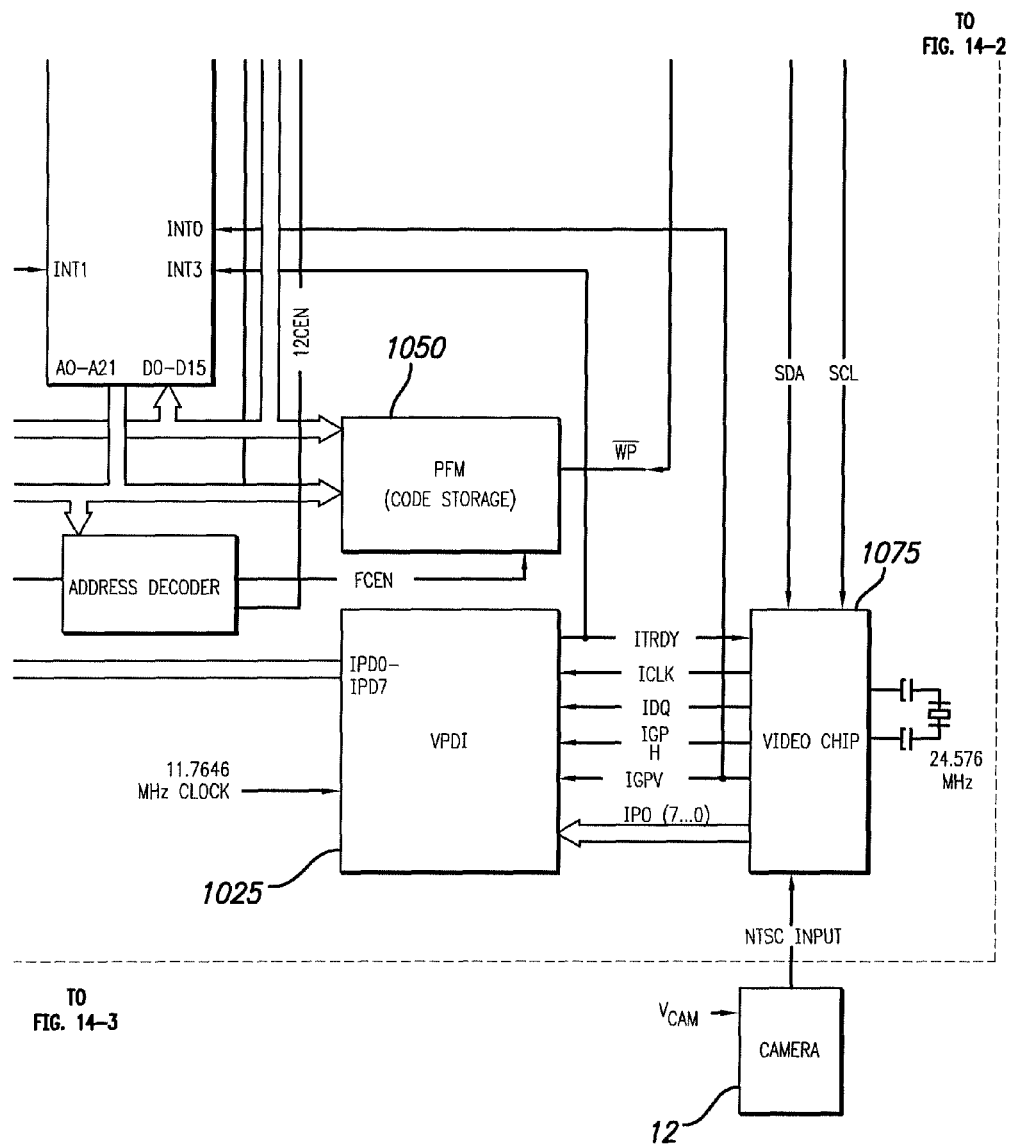

In one exemplary embodiment, the Fitting System shown in FIG. 9 may be used to configure system stimulation parameters and video processing strategies for each subject outfitted with the visual prosthesis apparatus of FIG. 1. The fitting application, operating system, laptops 10 and 30, isolation unit and VPU 20 may be tested and configuration controlled as a system. The software provides modules for electrode control, allowing an interactive construction of test stimuli with control over amplitude, pulse width, and frequency of the stimulation waveform of each electrode in the Retinal stimulation system 1. These parameters are checked to ensure that maximum charge per phase limits, charge balance, and power limitations are met before the test stimuli are presented to the subject. Additionally, these parameters may be checked a second time by the VPU 20's firmware. The Fitting System shown in FIG. 9 may also provide a psychophysics module for administering a series of previously determined test stimuli to record subject's responses. These responses may be indicated by a keypad 50 and or verbally. The psychophysics module may also be used to reliably measure perceptual parameters such as perceptual threshold, maximum comfort level, and spatial location of percepts. These perceptual parameters may be used to custom configure the transformation between the video image and spatio-tempral electrode stimulation parameters thereby optimizing the effectiveness of the visual prosthesis for each subject. The Fitting System is fully described in the related application U.S. application Ser. No. 11/796,425, filed on Apr. 27, 2007, which is incorporated herein by reference in its entirety.

Figure 10:
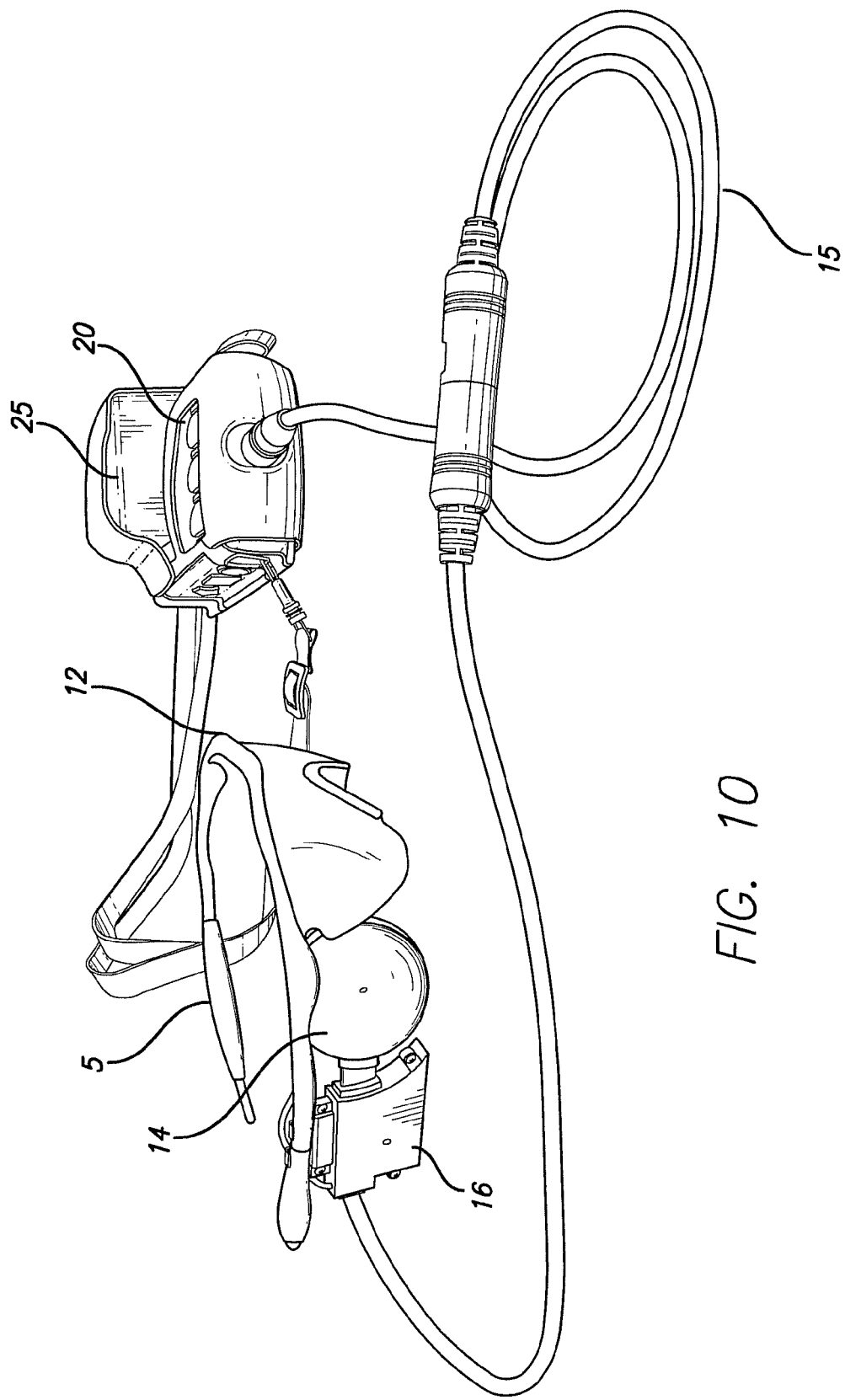
FIG. 10 shows the external portion of the visual prosthesis apparatus in a stand-alone mode, i.e. comprising the visor connected to a video processing unit.

The visual prosthesis apparatus may operate in two modes: i) stand-alone mode and ii) communication mode Stand-Alone Mode Referring to FIG. 10, in the stand-alone mode, the video camera 12, on the glasses 5, captures a video image that is sent to the VPU 20. The VPU 20 processes the image from the camera 12 and transforms it into electrical stimulation patterns that are transmitted to the external coil 14. The external coil 14 sends the electrical stimulation patterns and power via radio-frequency (RF) telemetry to the implanted retinal stimulation system. The internal coil 116 of the retinal stimulation system 1 receives the RF commands from the external coil 14 and transmits them to the electronics package 4 that in turn delivers stimulation to the retina via the electrode array 2. Additionally, the retinal stimulation system 1 may communicate safety and operational status back to the VPU 20 by transmitting RF telemetry from the internal coil 116 to the external coil 14. The visual prosthesis apparatus of FIG. 1 may be configured to electrically activate the retinal stimulation system 1 only when it is powered by the VPU 20 through the external coil 14. The stand-alone mode may be used for clinical testing and/or at-home use by the subject.

Communication Mode

The communication mode may be used for diagnostic testing, psychophysical testing, patient fitting and downloading of stimulation settings to the VPU 20 before transmitting data from the VPU 20 to the retinal stimulation system 1 as is done for example in the stand-alone mode described above. Referring to FIG. 9, in the communication mode, the VPU 20 is connected to the Fitting System laptop 10 using cables 70, 45 and the optically isolated serial connection adapter 40. In this mode, laptop 10 generated stimuli may be presented to the subject and programming parameters may be adjusted and downloaded to the VPU 20. The Psychophysical Test System (PTS) laptop 30 connected to the Fitting System laptop 10 may also be utilized to perform more sophisticated testing and analysis as fully described in the related application U.S. application Ser. No. 11/796,425, filed on Apr. 27, 2007, which is incorporated herein by reference in its entirety.

In one embodiment, the functionality of the retinal stimulation system can also be tested pre-operatively and intra-operatively (i.e. before operation and during operation) by using an external coil 14, without the glasses 5, placed in close proximity to the retinal stimulation system 1. The coil 14 may communicate the status of the retinal stimulation system 1 to the VPU 20 that is connected to the Fitting System laptop 10 as shown in FIG. 9.

As discussed above, the VPU 20 processes the image from the camera 12 and transforms the image into electrical stimulation patterns for the retinal stimulation system. Filters such as edge detection filters may be applied to the electrical stimulation patterns for example by the VPU 20 to generate, for example, a stimulation pattern based on filtered video data that the VPU 20 turns into stimulation data for the retinal stimulation system. The images may then be reduced in resolution using a downscaling filter. In one exemplary embodiment, the resolution of the image may be reduced to match the number of electrodes in the electrode array 2010 of the retinal stimulation system. That is, if the electrode array has, for example, sixty electrodes, the image may be reduced to a sixty channel resolution. After the reduction in resolution, the image is mapped to stimulation intensity using for example a look-up table that has been derived from testing of individual subjects. Then, the VPU 20 transmits the stimulation parameters via forward telemetry to the retinal stimulation system in frames that may employ a cyclic redundancy check (CRC) error detection scheme.

Figure 11:
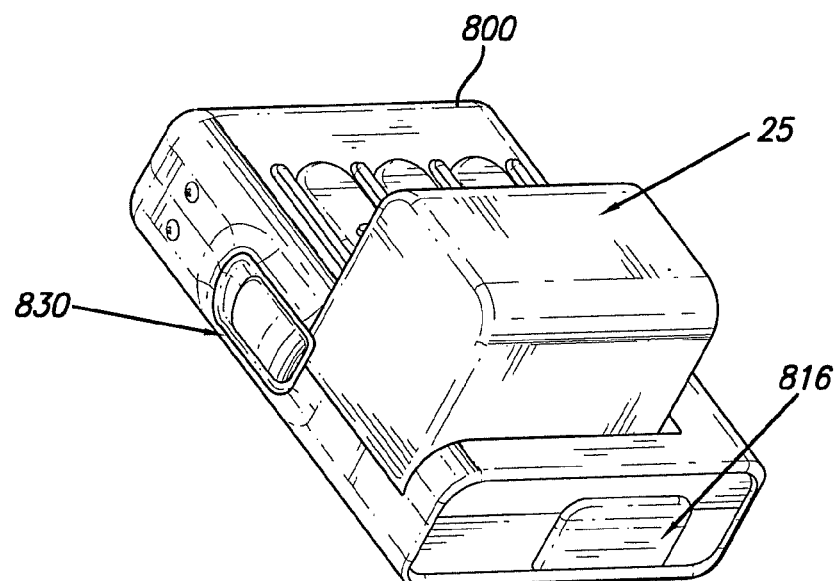
FIGS. 11-12 show the video processing unit in more detail already briefly shown with reference to FIGS. 9 and 10.
Figure 12:
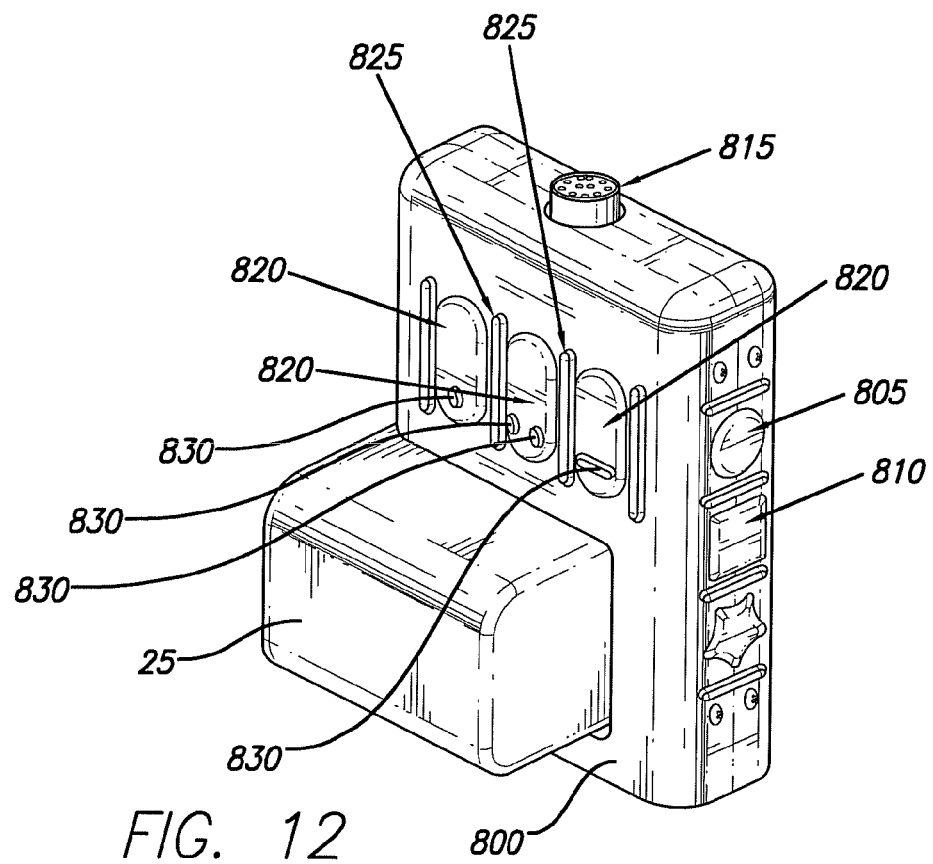

In one exemplary embodiment, the VPU 20 may be configured to allow the subject/patient i) to turn the visual prosthesis apparatus on and off, ii) to manually adjust settings, and iii) to provide power and data to the retinal stimulation system 1. Referring to FIGS. 11 and 12, the VPU 20 may comprise a case 800, power button 805 for turning the VPU 20 on and off, setting button 810, zoom buttons 820 for controlling the camera 12, connector port 815 for connecting to the Glasses 5, a connector port 816 for connecting to the laptop 10 through the connection adapter 40, indicator lights 825 to give visual indication of operating status of the system, the rechargeable battery 25 for powering the VPU 20, battery latch 830 for locking the battery 25 in the case 800, digital circuit boards (not shown), and a speaker (not shown) to provide audible alerts to indicate various operational conditions of the system. Because the VPU 20 is used and operated by a person with minimal or no vision, the buttons on the VPU 20 may be differently shaped and/or have special markings as shown in FIG. 12 to help the user identify the functionality of the button without having to look at it. As shown in FIG. 12, the power button 805 may be a circular shape while the settings button 820 may be square shape and the zoom buttons 820 may have special raised markings 830 to also identify each buttons functionality. One skilled in the art would appreciate that other shapes and markings can be used to identify the buttons without departing from the spirit and scope of the invention. For example, the markings can be recessed instead of raised.

In one embodiment, the indicator lights 825 may indicate that the VPU 20 is going through system start-up diagnostic testing when the one or more indicator lights 825 are blinking fast (more then once per second) and are green in color. The indicator lights 825 may indicate that the VPU 20 is operating normally when the one or more indicator lights 825 are blinking once per second and are green in color. The indicator lights 825 may indicate that the retinal stimulation system 1 has a problem that was detected by the VPU 20 at start-up diagnostic when the one or more indicator lights 825 are blinking for example once per five second and are green in color. The indicator lights 825 may indicate that the video signal from camera 12 is not being received by the VPU 20 when the one or more indicator lights 825 are always on and are amber color. The indicator lights 825 may indicate that there is a loss of communication between the retinal stimulation system 1 and the external coil 14 due to the movement or removal of Glasses 5 while the system is operational or if the VPU 20 detects a problem with the retinal stimulation system 1 and shuts off power to the retinal stimulation system 1 when the one or more indicator lights 825 are always on and are orange color. One skilled in the art would appreciate that other colors and blinking patterns can be used to give visual indication of operating status of the system without departing from the spirit and scope of the invention.

In one embodiment, a single short beep from the speaker (not shown) may be used to indicate that one of the buttons 825, 805 or 810 have been pressed. A single beep followed by two more beeps from the speaker (not shown) may be used to indicate that VPU 20 is turned off. Two beeps from the speaker (not shown) may be used to indicate that VPU 20 is starting up. Three beeps from the speaker (not shown) may be used to indicate that an error has occurred and the VPU 20 is about to shut down automatically. As would be clear to one skilled in the are different periodic beeping may also be used to indicate a low battery voltage warning, that there is a problem with the video signal, and/or there is a loss of communication between the retinal stimulation system 1 and the external coil 14. One skilled in the art would appreciate that other sounds can be used to give audio indication of operating status of the system without departing from the spirit and scope of the invention. For example, the beeps may be replaced by an actual prerecorded voice indicating operating status of the system.

In one exemplary embodiment, the VPU 20 is in constant communication with the retinal stimulation system through forward and backward telemetry. In this document, the forward telemetry refers to transmission from VPU 20 to the retinal stimulation system 1 and the backward telemetry refers to transmissions from the Retinal stimulation system 1 to the VPU 20. During the initial setup, the VPU 20 may transmit null frames (containing no stimulation information) until the VPU 20 synchronizes with the Retinal stimulation system 1 via the back telemetry. In one embodiment, an audio alarm may be used to indicate whenever the synchronization has been lost.

In order to supply power and data to the Retinal stimulation system 1, the VPU 20 may drive the external coil 14, for example, with a 3 MHz signal. To protect the subject, the retinal stimulation system 1 may comprise a failure detection circuit to detect direct current leakage and to notify the VPU 20 through back telemetry so that the visual prosthesis apparatus can be shut down.

The forward telemetry data (transmitted for example at 122.76 kHz) may be modulated onto the exemplary 3 MHz carrier using Amplitude Shift Keying (ASK), while the back telemetry data (transmitted for example at 3.8 kHz) may be modulated using Frequency Shift Keying (FSK) with, for example, 442 kHz and 457 kHz. The theoretical bit error rates can be calculated for both the ASK and FSK scheme assuming a ratio of signal to noise (SNR). The system disclosed in the present disclosure can be reasonably expected to see bit error rates of 10-5 on forward telemetry and 10-3 on back telemetry. These errors may be caught more than 99.998% of the time by both an ASIC hardware telemetry error detection algorithm and the VPU 20's firmware. For the forward telemetry, this is due to the fact that a 16-bit cyclic redundancy check (CRC) is calculated for every 1024 bits sent to the ASIC within electronics package 4 of the Retinal Stimulation System 1. The ASIC of the Retinal Stimulation System 1 verifies this CRC and handles corrupt data by entering a non-stimulating 'safe' state and reporting that a telemetry error was detected to the VPU 20 via back telemetry. During the 'safe' mode, the VPU 20 may attempt to return the implant to an operating state. This recovery may be on the order of milliseconds.

The back telemetry words are checked for a 16-bit header and a single parity bit. For further protection against corrupt data being misread, the back telemetry is only checked for header and parity if it is recognized as properly encoded Bi-phase Mark Encoded (BPM) data. If the VPU 20 detects invalid back telemetry data, the VPU 20 immediately changes mode to a 'safe' mode where the Retinal Stimulation System 1 is reset and the VPU 20 only sends non-stimulating data frames. Back telemetry errors cannot cause the VPU 20 to do anything that would be unsafe.

Figure 13A:
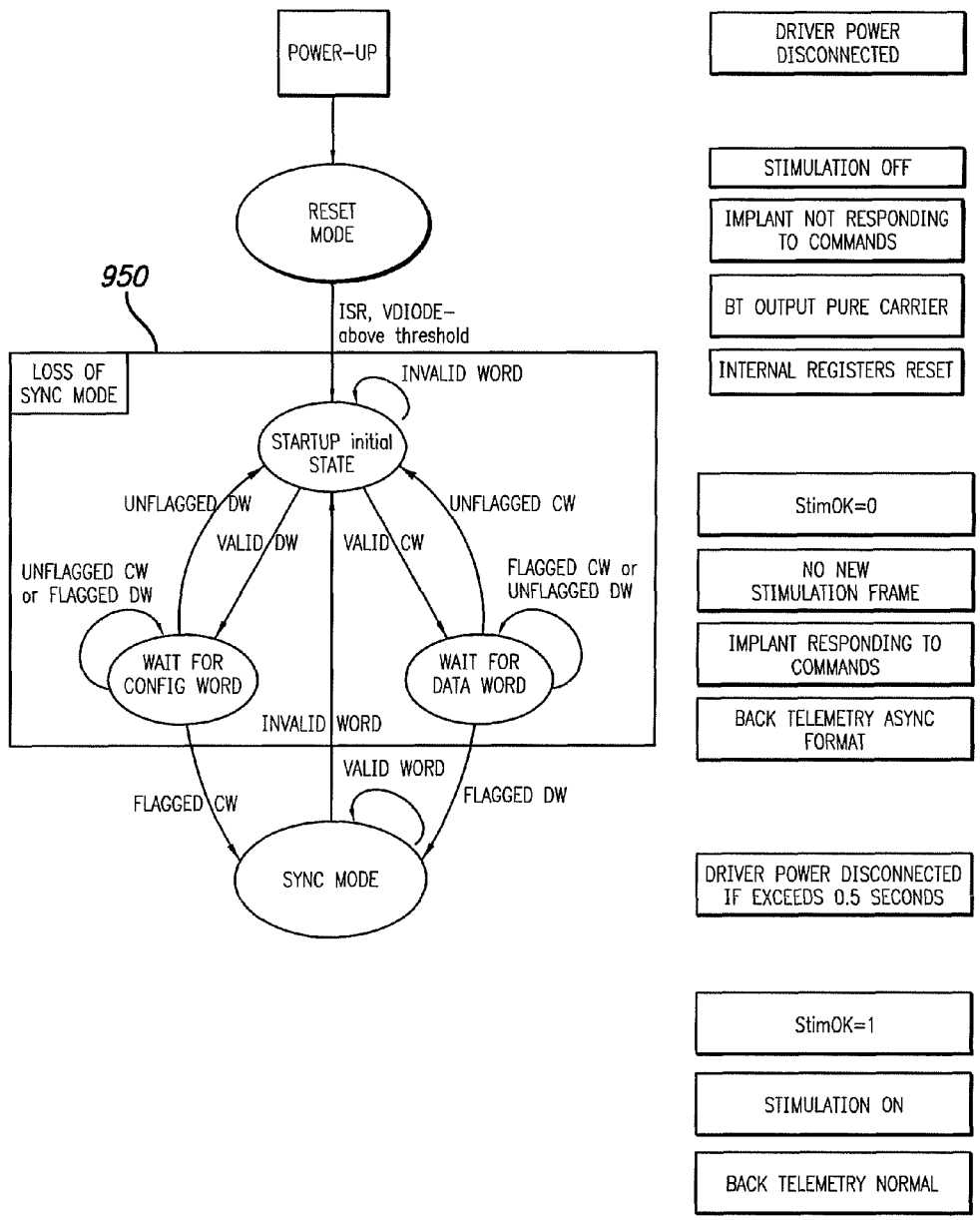
FIG. 13a shows a LOSS OF SYNC mode.

The response to errors detected in data transmitted by VPU 20 may begin at the ASIC of the Retinal Stimulation System 1. The Retinal Stimulation System 1 may be constantly checking the headers and CRCs of incoming data frames. If either the header or CRC check fails, the ASIC of the Retinal Stimulation System 1 may enter a mode called LOSS OF SYNC 950, shown in FIG. 13a. In LOSS OF SYNC mode 950, the Retinal Stimulation System 1 will no longer produce a stimulation output, even if commanded to do so by the VPU 20. This cessation of stimulation occurs after the end of the stimulation frame in which the LOSS OF SYNC mode 950 is entered, thus avoiding the possibility of unbalanced pulses not completing stimulation. If the Retinal Stimulation System 1 remains in a LOSS OF SYNC mode 950 for 1 second or more (for example, caused by successive errors in data transmitted by VPU 20), the ASIC of the Retinal Stimulation System 1 disconnects the power lines to the stimulation pulse drivers. This eliminates the possibility of any leakage from the power supply in a prolonged LOSS OF SYNC mode 950. From the LOSS OF SYNC mode 950, the Retinal Stimulation System 1 will not re-enter a stimulating mode until it has been properly initialized with valid data transmitted by the VPU 20.

In addition, the VPU 20 may also take action when notified of the LOSS OF SYNC mode 950. As soon as the Retinal Stimulation System 1 enters the LOSS OF SYNC mode 950, the Retinal Stimulation System 1 reports this fact to the VPU 20 through back telemetry. When the VPU 20 detects that the Retinal Stimulation System 1 is in LOSS OF SYNC mode 950, the VPU 20 may start to send 'safe' data frames to the Retinal Stimulation System 1. 'Safe' data is data in which no stimulation output is programmed and the power to the stimulation drivers is also programmed to be off. The VPU 20 will not send data frames to the Retinal Stimulation System 1 with stimulation commands until the VPU 20 first receives back telemetry from the Retinal Stimulation System 1 indicating that the Retinal Stimulation System 1 has exited the LOSS OF SYNC mode 950. After several unsuccessful retries by the VPU 20 to take the implant out of LOSS OF SYNC mode 950, the VPU 20 will enter a Low Power Mode (described below) in which the implant is only powered for a very short time. In this time, the VPU 20 checks the status of the implant. If the implant continues to report a LOSS OF SYNC mode 950, the VPU 20 turns power off to the Retinal Stimulation System 1 and tries again later. Since there is no possibility of the implant electronics causing damage when it is not powered, this mode is considered very safe.

Due to an unwanted electromagnetic interference (EMI) or electrostatic discharge (ESD) event the VPU 20 data, specifically the VPU firmware code, in RAM can potentially get corrupted and may cause the VPU 20 firmware to freeze. As a result, the VPU 20 firmware will stop resetting the hardware watchdog circuit, which may cause the system to reset. This will cause the watchdog timer to expire causing a system reset in, for example, less than 2.25 seconds. Upon recovering from the reset, the VPU 20 firmware logs the event and shuts itself down. VPU 20 will not allow system usage after this occurs once. This prevents the VPU 20 code from freezing for extended periods of time and hence reduces the probability of the VPU sending invalid data frames to the implant.

Supplying power to the Retinal stimulation system 1 can be a significant portion of the VPU 20's total power consumption. When the Retinal stimulation system 1 is not within receiving range to receive either power or data from the VPU 20, the power used by the VPU 20 is wasted.

Power delivered to the Retinal stimulation system 1 may be dependant on the orientation of the coils 14 and 116. The power delivered to the Retinal stimulation system 1 may be controlled, for example, via the VPU 20 every 16.6 ms. The Retinal stimulation system 1 may report how much power it receives and the VPU 20 may adjust the power supply voltage of the RF driver to maintain a required power level on the Retinal stimulation system 1. Two types of power loss may occur: 1) long term (>~1 second) and 2) short term (<~1 second). The long term power loss may be caused, for example, by a subject removing the Glasses 5.

Figure 13B:
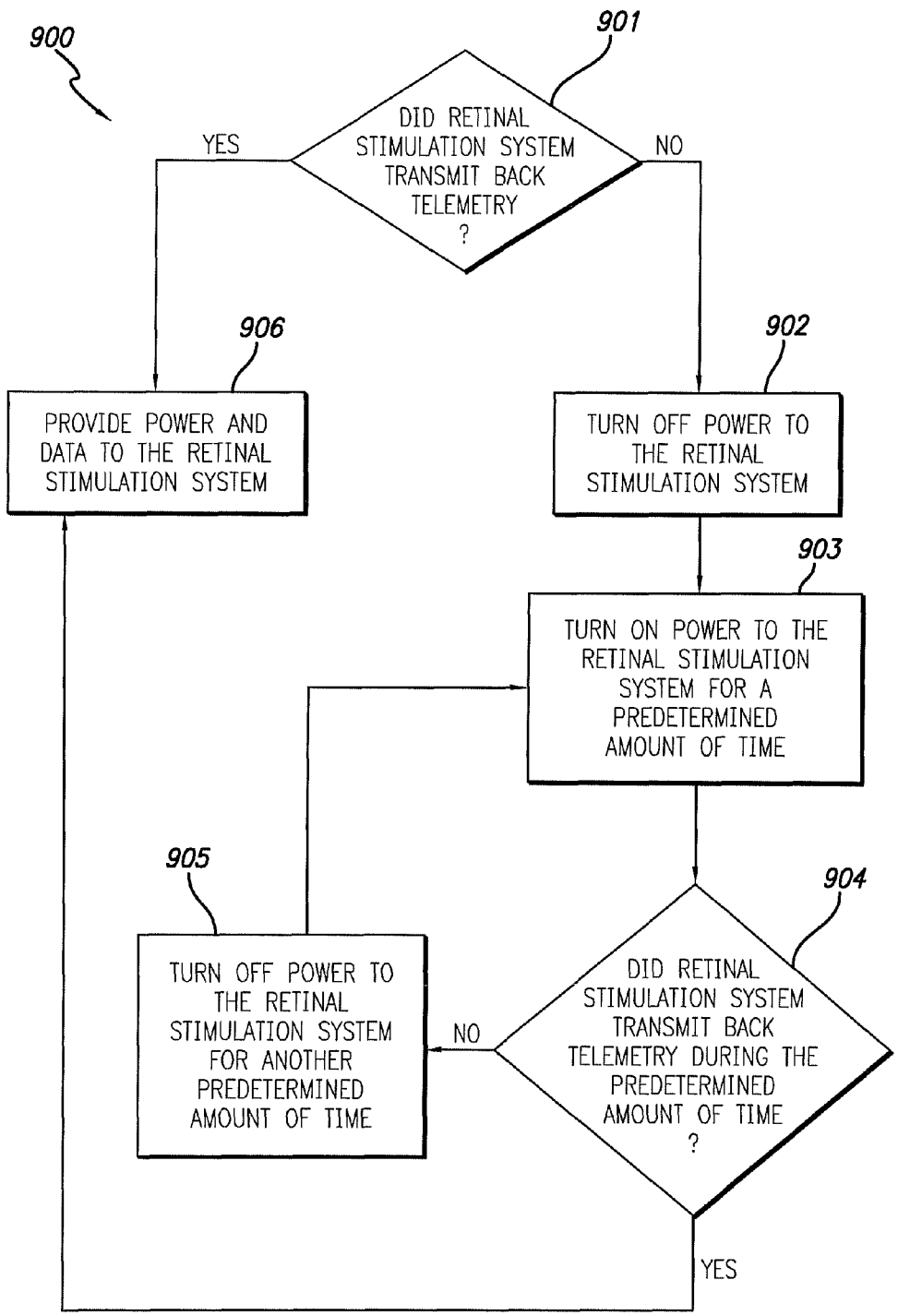
FIG. 13b shows an exemplary block diagram of the steps taken when VPU does not receive back telemetry from the Retinal stimulation system.

In one exemplary embodiment, the Low Power Mode may be implemented to save power for VPU 20. The Low Power Mode may be entered, for example, anytime the VPU 20 does not receive back telemetry from the Retinal stimulation system 1. Upon entry to the Low Power Mode, the VPU 20 turns off power to the Retinal stimulation system 1. After that, and periodically, the VPU 20 turns power back on to the Retinal stimulation system 1 for an amount of time just long enough for the presence of the Retinal stimulation system 1 to be recognized via its back telemetry. If the Retinal stimulation system 1 is not immediately recognized, the controller again shuts off power to the Retinal stimulation system 1. In this way, the controller 'polls' for the passive Retinal stimulation system 1 and a significant reduction in power used is seen when the Retinal stimulation system 1 is too far away from its controller device. FIG. 13*b* depicts an exemplary block diagram 900 of the steps taken when the VPU 20 does not receive back telemetry from the Retinal stimulation system 1. If the VPU 20 receives back telemetry from the Retinal stimulation system 1 (output "YES" of step 901), the Retinal stimulation system 1 may be provided with power and data (step 906). If the VPU 20 does not receive back telemetry from the Retinal stimulation system 1 (output "NO" of step 901), the power to the Retinal stimulation system 1 may be turned off After some amount of time, power to the Retinal stimulation system 1 may be turned on again for enough time to determine if the Retinal stimulation system 1 is again transmitting back telemetry (step 903). If the Retinal stimulation system 1 is again transmitting back telemetry (step 904), the Retinal stimulation system 1 is provided with power and data (step 906). If the Retinal stimulation system 1 is not transmitting back telemetry (step 904), the power to the Retinal stimulation system 1 may again be turned off for a predetermined amount of time (step 905) and the process may be repeated until the Retinal stimulation system 1 is again transmitting back telemetry.

Figure 13C:
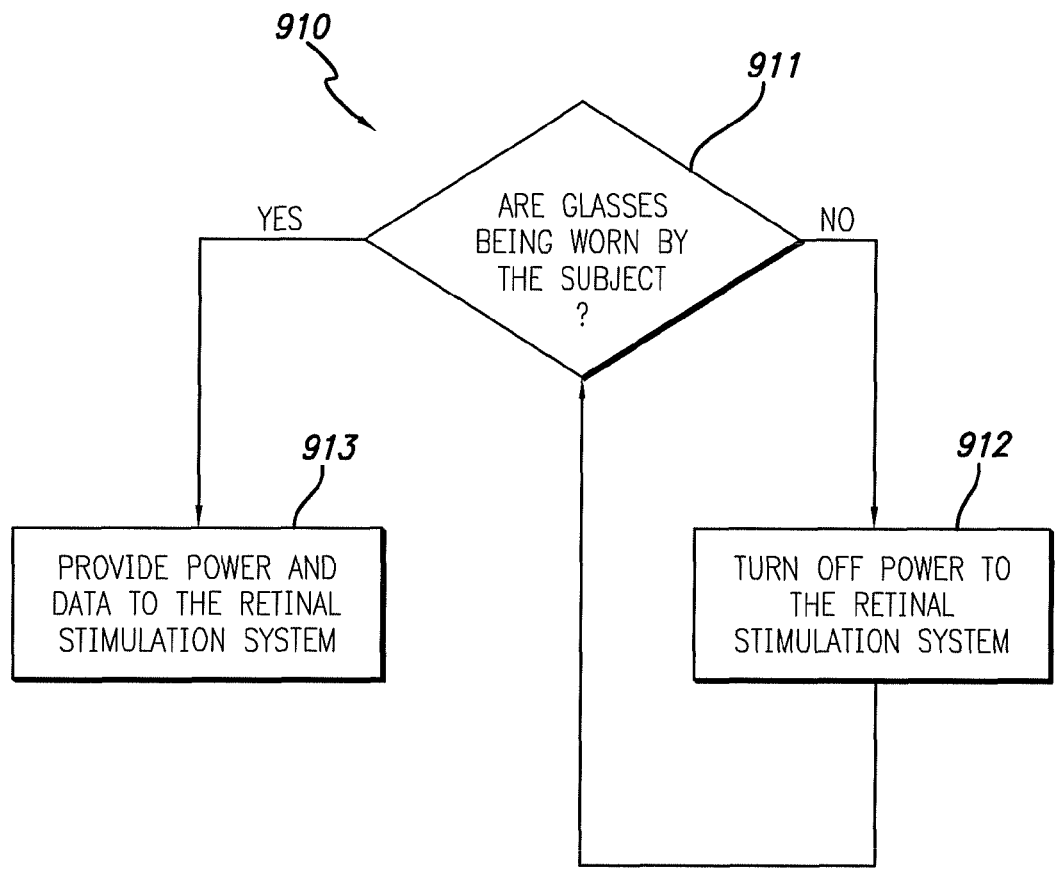
FIG. 13c shows an exemplary block diagram of the steps taken when the subject is not wearing Glasses.

In another exemplary embodiment, the Low Power Mode may be entered whenever the subject is not wearing the Glasses 5. In one example, the Glasses 5 may contain a capacitive touch sensor (not shown) to provide the VPU 20 digital information regarding whether or not the Glasses 5 are being worn by the subject. In this example, the Low Power Mode may be entered whenever the capacitive touch sensor detects that the subject is not wearing the Glasses 5. That is, if the subject removes the Glasses 5, the VPU 20 will shut off power to the external coil 14. As soon as the Glasses 5 are put back on, the VPU 20 will resume powering the external coil 14. FIG. 13*c* depicts an exemplary block diagram 910 of the steps taken when the capacitive touch sensor detects that the subject is not wearing the Glasses 5. If the subject is wearing Glasses 5 (step 911), the Retinal stimulation system 1 is provided with power and data (step 913). If the subject is not wearing Glasses 5 (step 911), the power to the Retinal stimulation system 1 is turned off (step 912) and the process is repeated until the subject is wearing Glasses 5.

One exemplary embodiment of the VPU 20 is shown in FIG. 14. The VPU 20 may comprise: a Power Supply, a Distribution and Monitoring Circuit (PSDM) 1005, a Reset Circuit 1010, a System Main Clock (SMC) source (not shown), a Video Preprocessor Clock (VPC) source (not shown), a Digital Signal Processor (DSP) 1020, Video Preprocessor Data Interface 1025, a Video Preprocessor 1075, an I$^2$C Protocol Controller 1030, a Complex Programmable Logic device (CPLD) (not shown), a Forward Telemetry Controller (FTC) 1035, a Back Telemetry Controller (BTC) 1040, Input/Output Ports 1045, Memory Devices like a Parallel Flash Memory (PFM) 1050 and a Serial Flash Memory (SFM) 1055, a Real Time Clock 1060, an RF Voltage and Current Monitoring Circuit (VIMC) (not shown), a speaker and/or a buzzer, an RF receiver 1065, and an RF transmitter 1070.

The Power Supply, Distribution and Monitoring Circuit (PSDM) 1005 may regulate a variable battery voltage to several stable voltages that apply to components of the VPU 20. The Power Supply, Distribution and Monitoring Circuit (PSDM) 1005 may also provide low battery monitoring and depleted battery system cutoff. The Reset Circuit 1010 may have reset inputs 1011 that are able to invoke system level rest. For example, the reset inputs 1011 may be from a manual push-button reset, a watchdog timer expiration, and/or firmware based shutdown. The System Main Clock (SMC) source is a clock source for DSP 1020 and CPLD. The Video Preprocessor Clock (VPC) source is a clock source for the Video Processor. The DSP 1020 may act as the central processing unit of the VPU 20. The DSP 1020 may communicate with the rest of the components of the VPU 20 through parallel and serial interfaces. The Video Processor 1075 may convert the NTSC signal from the camera 12 into a down-scaled resolution digital image format. The Video Processor 1075 may comprise a video decoder (not shown) for converting the NTSC signal into high-resolution digitized image and a video scaler (not shown) for scaling down the high-resolution digitized image from the video decoder to an intermediate digitized image resolution. The video decoder may be composed of an Analog Input Processing, Chrominance and Luminance Processing and Brightness Contrast and Saturation (BSC) Control circuits. The video scaler may be composed of Acquisition control, Pre-scaler, BSC-control, Line Buffer and Output Interface. The I²C Protocol Controller 1030 may serve as a link between the DSP 1020 and the I²C bus. The I²C Protocol Controller 1030 may be able to convert the parallel bus interface of the DSP 1020 to the I²C protocol bus or vise versa. The I²C Protocol Controller 1030 may also be connected to the Video Processor 1075 and the Real Time Clock 1060. The VPDI 1025 may contain a tri-state machine to shift video data from Video Preprocessor 1075 to the DSP 1020. The Forward Telemetry Controller (FTC) 1035 packs 1024 bits of forward telemetry data into a forward telemetry frame. The FTC 1035 retrieves the forward telemetry data from the DSP 1020 and converts the data from logic level to biphase marked data. The Back Telemetry Controller (BTC) 1040 retrieves the biphase marked data from the RF receiver 1065, decodes it, and generates the BFSR and BCLKR for the DSP 1020. The Input/Output Ports 1045 provide expanded JO functions to access the CPLD on-chip and off-chip devices. The Parallel Flash Memory (PFM) 1050 may be used to store executable code and the Serial Flash Memory (SFM) 1055 may provide Serial Port Interface (SPI) for data storage. The VIMC may be used to sample and monitor RF transmitter 1070 current and voltage in order to monitor the integrity status of the retinal stimulation system 1.

FIG. 16 shows a perspective view of the implanted portion of the preferred visual prosthesis. A flexible circuit 2001 includes a flexible circuit electrode array 2010 which is mounted by a retinal tack (not shown) or similar means to the epiretinal surface. The flexible circuit electrode array 2010 is electrically coupled by a flexible circuit cable 2012, which pierces the sclera and is electrically coupled to an electronics package 2014, external to the sclera.

The electronics package 2014 is electrically coupled to a secondary inductive coil 2016. Preferably the secondary inductive coil 2016 is made from wound wire. Alternatively, the secondary inductive coil 2016 may be made from a flexible circuit polymer sandwich with wire traces deposited between layers of flexible circuit polymer. The secondary inductive coil receives power and data from a primary inductive coil 2017, which is external to the body. The electronics package 2014 and secondary inductive coil 2016 are held together by the molded body 2018. The molded body 18 holds the electronics package 2014 and secondary inductive coil 16 end to end. The secondary inductive coil 16 is placed around the electronics package 2014 in the molded body 2018. The molded body 2018 holds the secondary inductive coil 2016 and electronics package 2014 in the end to end orientation and minimizes the thickness or height above the sclera of the entire device. The molded body 2018 may also include suture tabs 2020. The molded body 2018 narrows to form a strap 2022 which surrounds the sclera and holds the molded body 2018, secondary inductive coil 2016, and electronics package 2014 in place. The molded body 2018, suture tabs 2020 and strap 2022 are preferably an integrated unit made of silicone elastomer. Silicone elastomer can be formed in a pre-curved shape to match the curvature of a typical sclera. However, silicone remains flexible enough to accommodate implantation and to adapt to variations in the curvature of an individual sclera. The secondary inductive coil 2016 and molded body 2018 are preferably oval shaped. A strap 2022 can better support an oval shaped coil. It should be noted that the entire implant is attached to and supported by the sclera. An eye moves constantly. The eye moves to scan a scene and also has a jitter motion to improve acuity. Even though such motion is useless in the blind, it often continues long after a person has lost their sight. By placing the device under the rectus muscles with the electronics package in an area of fatty tissue between the rectus muscles, eye motion does not cause any flexing which might fatigue, and eventually damage, the device.

Figure 17:
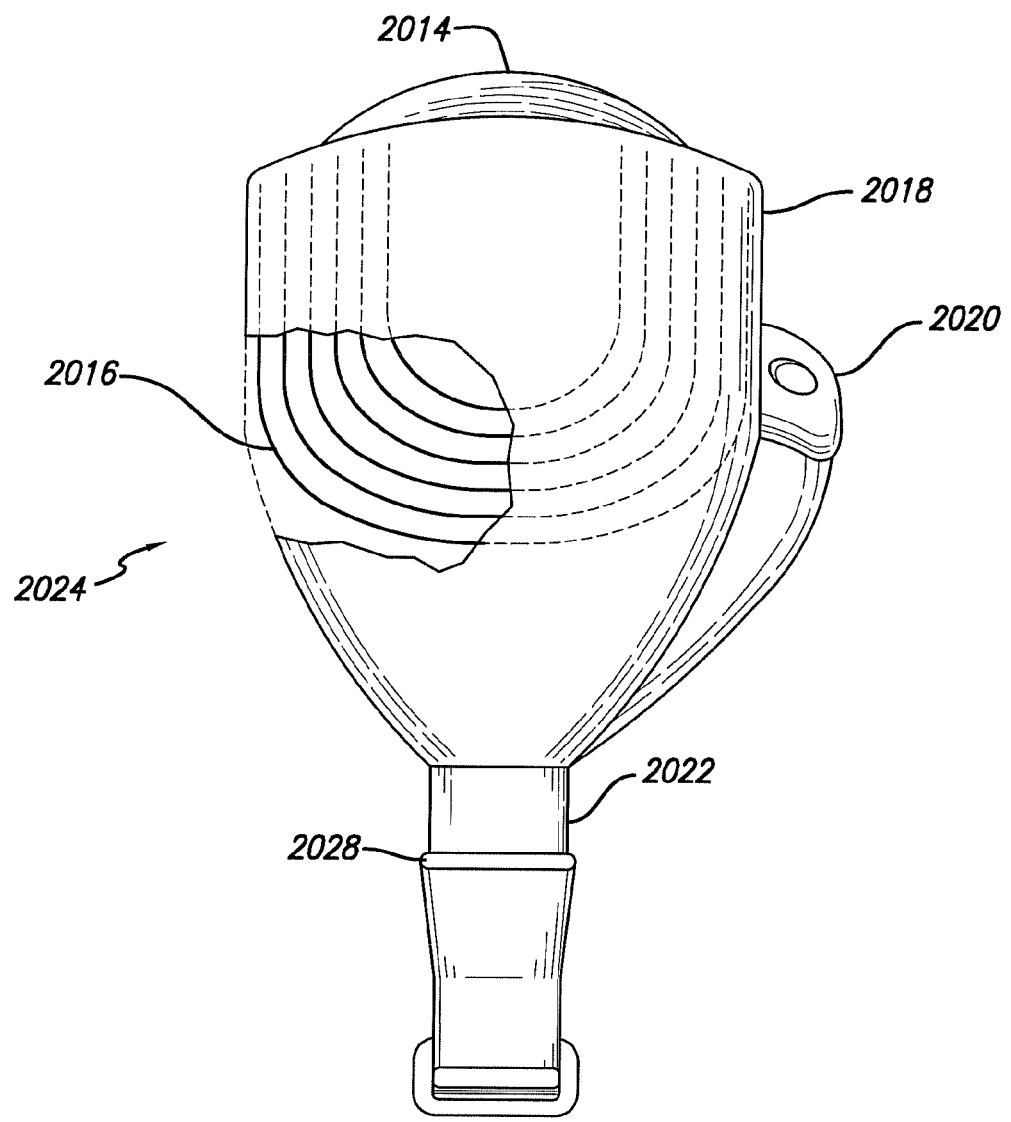
FIG. 17 is a side view of the implanted portion of the preferred visual prosthesis showing the fan tail in more detail.

FIG. 17 shows a side view of the implanted portion of the visual prosthesis, in particular, emphasizing the fan tail 2024. When implanting the visual prosthesis, it is necessary to pass the strap 2022 under the eye muscles to surround the sclera. The secondary inductive coil 2016 and molded body 2018 must also follow the strap 2022 under the lateral rectus muscle on the side of the sclera. The implanted portion of the visual prosthesis is very delicate. It is easy to tear the molded body 2018 or break wires in the secondary inductive coil 2016. In order to allow the molded body 18 to slide smoothly under the lateral rectus muscle, the molded body 2018 is shaped in the form of a fan tail 2024 on the end opposite the electronics package 2014. The strap 2022 further includes a hook 2028 the aids the surgeon in passing the strap under the rectus muscles.

Figure 18:
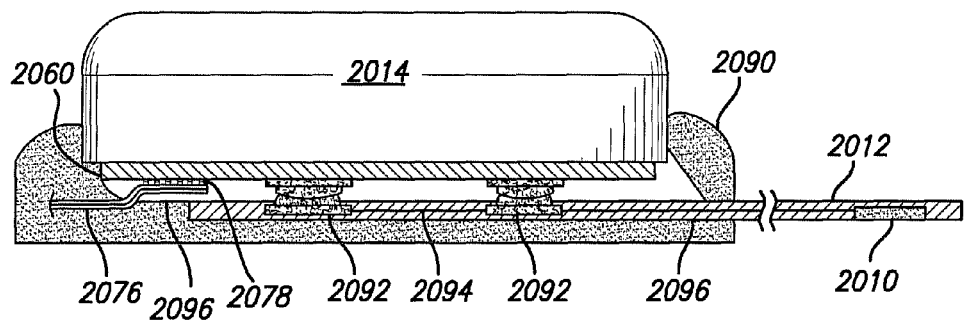
FIG. 18 is a view of the completed package attached to an electrode array.

Referring to FIG. 18, the flexible circuit 1, includes platinum conductors 2094 insulated from each other and the external environment by a biocompatible dielectric polymer 2096, preferably polyimide. One end of the array contains exposed electrode sites that are placed in close proximity to the retinal surface 2010. The other end contains bond pads 2092 that permit electrical connection to the electronics package 2014. The electronic package 2014 is attached to the flexible circuit 1 using a flip-chip bumping process, and epoxy underfilled. In the flip-chip bumping process, bumps containing conductive adhesive placed on bond pads 2092 and bumps containing conductive adhesive placed on the electronic package 2014 are aligned and melted to build a conductive connection between the bond pads 2092 and the electronic package 2014. Leads 2076 for the secondary inductive coil 2016 are attached to gold pads 2078 on the ceramic substrate 2060 using thermal compression bonding, and are then covered in epoxy. The electrode array cable 2012 is laser welded to the assembly junction and underfilled with epoxy. The junction of the secondary inductive coil 2016, array 2001, and electronic package 2014 are encapsulated with a silicone overmold 2090 that connects them together mechanically. When assembled, the hermetic electronics package 2014 sits about 3 mm away from the end of the secondary inductive coil.

Since the implant device is implanted just under the conjunctiva it is possible to irritate or even erode through the conjunctiva. Eroding through the conjunctiva leaves the body open to infection. We can do several things to lessen the likelihood of conjunctiva irritation or erosion. First, it is important to keep the over all thickness of the implant to a minimum. Even though it is advantageous to mount both the electronics package 2014 and the secondary inductive coil 2016 on the lateral side of the sclera, the electronics package 2014 is mounted higher than, but not covering, the secondary inductive coil 2016. In other words the thickness of the secondary inductive coil 2016 and electronics package should not be cumulative.

It is also advantageous to place protective material between the implant device and the conjunctiva. This is particularly important at the scleratomy, where the thin film electrode array cable 2012 penetrates the sclera. The thin film electrode array cable 2012 must penetrate the sclera through the pars plana, not the retina. The scleratomy is, therefore, the point where the device comes closest to the conjunctiva. The protective material can be provided as a flap attached to the implant device or a separate piece placed by the surgeon at the time of implantation. Further material over the scleratomy will promote healing and sealing of the scleratomy. Suitable materials include DACRON®, TEFLON®, GORETEX® (ePTFE), TUTOPLAST® (sterilized sclera), MERSILENE® (polyester) or silicone.

Figure 19:
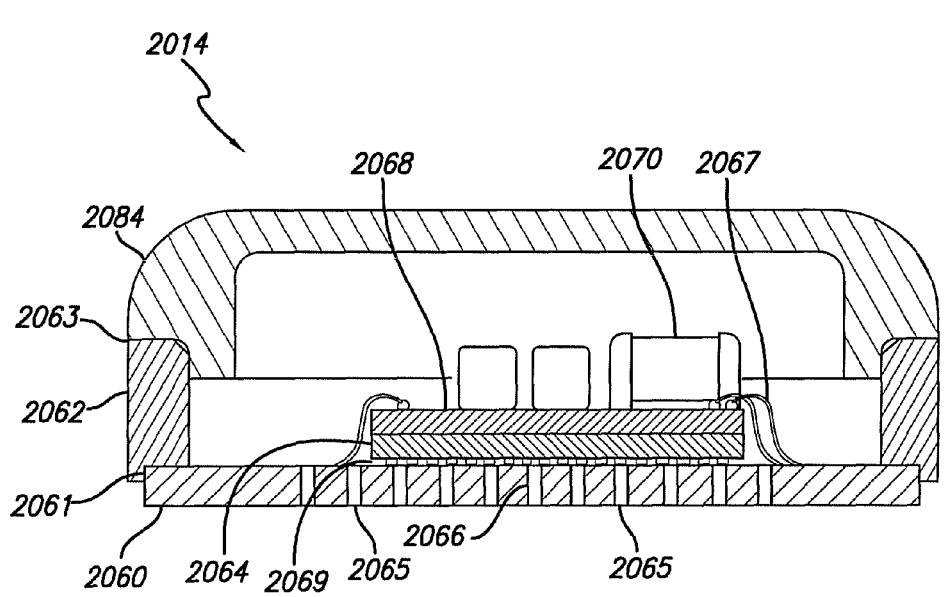
FIG. 19 is a cross-section of the package.

Referring to FIG. 19, the package 2014 contains a ceramic substrate 2060, with metalized vias 2065 and thin-film metallization 2066. The package 2014 contains a metal case wall 2062 which is connected to the ceramic substrate 2060 by braze joint 2061. On the ceramic substrate 2060 an underfill 2069 is applied. On the underfill 69 an integrated circuit chip 2064 is positioned. On the integrated circuit chip 2064 a ceramic hybrid substrate 2068 is positioned. On the ceramic hybrid substrate 2068 passives 2070 are placed. Wirebonds 2067 are leading from the ceramic substrate 2060 to the ceramic hybrid substrate 2068. A metal lid 2084 is connected to the metal case wall 2062 by laser welded joint 2063 whereby the package 2014 is sealed.

Figure 20:
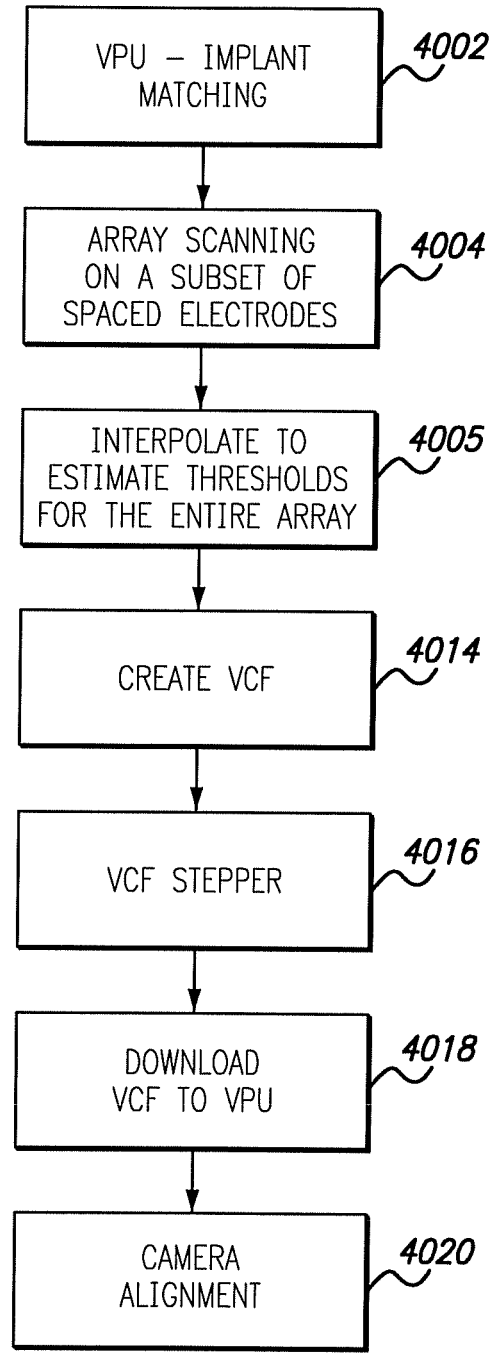
FIG. 20 is a flow chart of an alternate embodiment of fast fitting.

Referring to FIG. 20, fast fitting is a variation of the hybrid fitting to obtain a quick fit to allow use of the visual prosthesis. The fast fitting can be follow up with a full hybrid fit.

The fast fitting process begins with video processing unit (VPU) implant matching. 4002. This automatically checks to insure that the VPU and the video configuration file (VCF) stored on the VPU are properly matched to the implant and not confused with another implant. The next step is array scanning on single electrodes 4004. In the preferred embodiment 18 out of 60 electrodes are tested. It should be clear that other numbers may be selected particularly with a larger array of electrodes. The point is that it is a subset of all the electrodes. Results from the subset are interpolated to the remaining electrodes 4005. Then a VCF is created from the threshold data 4014, the VPU is stepped 4018, and the VCF is loaded on the VPU 4018. The final step is camera alignment 4020.

Referring to FIGS. 21A and 21B, the fast fitting is not as accurate as hybrid fitting but is close. These graphs show fit data for two test subjects. Fast fit points 4022 are show with a circle with an outline and x. full fit data points 4024 are shown with a circle. The data is then interpolated in lines 4026 for fast fit data and 4028 for full fit data. Results are similar.

Accordingly, what has been shown is an improved visual prosthesis and an improved method for limiting power consumption in a visual prosthesis. While the invention has been described by means of specific embodiments and applications thereof, it is understood that numerous modifications and variations could be made thereto by those skilled in the art without departing from the spirit and scope of the invention. It is therefore to be understood that within the scope of the claims, the invention may be practiced otherwise than as specifically described herein.

The invention claimed is:

1. A method of brightness fitting a visual prosthesis comprising:
   a. providing an array of electrodes suitable to contact visual neural tissue;
   b. activating a prompt;
   c. activating a signal at a level on a selected electrode within a subset of the array of electrodes;
   d. receiving a yes response from a subject indicating a visual perception at a threshold brightness level or a no response from the subject indicating no visual perception;
   e. recording the yes or no response;
   f. applying a predetermined computer algorithm which predicts a confidence of a correct answer based upon consistency of previous answers to determine a next activation level on the selected electrode; and
   g. repeating steps b through f until the electrode is fit; and
   h. repeating the steps b through g for each electrode in the subset.

2. The method according to claim 1, wherein the signal is a signal on an individual electrode.

3. The method according to claim 1, wherein the signal is a signal on a plurality of electrodes.

4. The method according to claim 3, wherein the plurality is four.

5. The method according to claim 1, wherein the prompt is an audio prompt.

6. The method according to claim 1, wherein the step of activating a signal includes activating no signal at a pseudorandom interval.

7. The method according to claim 1, wherein the predetermined algorithm is a maximum likelihood algorithm.

8. The method according to claim 7, wherein the maximum likelihood algorithm is according to the equation $$L_i = \prod_{q=1}^{m} (p_{q,i})^{n_{yes,q}} \cdot (1 - p_{q,i})^{n_{no,q}}$$

Where:
   $L_i$ is the likelihood that the threshold value is at level i
   $p_{q,i}$ is the probability, according to the Psychometric Function, that the patient will perceive a stimulation at level q given that the threshold is at level i
   $n_{yes,q}$ is the number of Yes responses in all previous presentations (trials) at level q
   $n_{no,q}$ is the number of No responses in all previous presentations (trials) at level q
   m is the number of levels in the range—the highest level.

9. A method of fitting a visual prosthesis comprising:
   a. providing an array of electrodes suitable to contact visual neural tissue;
   b. activating a prompt;
   c. activating a signal on an electrode within a subset of the array of electrodes;
   d. receiving a response from a subject indicating a visual perception;
   e. recording the response;
   f. repeating steps b through e for each electrode in the subset;
   g. interpolating responses on electrodes not in the subset; and
   h. applying a predetermined algorithm which predicts a confidence of a correct answer based upon consistency of previous answers to determine a next activation signal.

10. The method according to claim 9, wherein the prompt is an audio prompt.

11. The method according to claim 9, wherein the step of activating a signal includes activating no signal at a pseudorandom interval.

* * * * *